US007767799B2

(12) United States Patent
Schreiber et al.

(10) Patent No.: US 7,767,799 B2
(45) Date of Patent: Aug. 3, 2010

(54) NUCLEIC ACID MOLECULES ENCODING RECOMBINANT INTERFERON-α2 (IFNα2) MUTANTS

(75) Inventors: Gideon E Schreiber, Rehovot (IL); Laila C. Roisman, Tel Aviv (IL); Diego Jaitin, Rehovot (IL); Eyal Kalie, Hod Hasharon (IL)

(73) Assignee: Yeda Research and Development Co. Ltd. at the Weizmann Institute of Science, Rehovot (IL)

( * ) Notice: Subject to any disclaimer, the term of this patent is extended or adjusted under 35 U.S.C. 154(b) by 0 days.

(21) Appl. No.: 11/994,159

(22) PCT Filed: Jun. 28, 2006

(86) PCT No.: PCT/IL2006/000754
§ 371 (c)(1),
(2), (4) Date: Apr. 30, 2008

(87) PCT Pub. No.: WO2007/000769
PCT Pub. Date: Jan. 4, 2007

(65) Prior Publication Data
US 2008/0279823 A1 Nov. 13, 2008

Related U.S. Application Data

(60) Provisional application No. 60/694,810, filed on Jun. 29, 2005.

(51) Int. Cl.
C07H 21/04 (2006.01)
(52) U.S. Cl. .................................. 536/23.52
(58) Field of Classification Search ....................... None
See application file for complete search history.

(56) References Cited

U.S. PATENT DOCUMENTS

| 4,588,585 | A | 5/1986 | Mark et al. | 424/85 |
|---|---|---|---|---|
| 4,766,106 | A | 8/1988 | Katre et al. | 514/12 |
| 4,917,888 | A | 4/1990 | Katre et al. | 424/85.91 |
| 5,382,657 | A | 1/1995 | Karasiewicz et al. | 530/351 |
| 5,609,868 | A | 3/1997 | Lowther et al. | 424/857 |
| 6,214,966 | B1 | 4/2001 | Harris | 528/322 |
| 7,141,547 | B2* | 11/2006 | Rosen et al. | 514/12 |
| 7,456,257 | B2 | 11/2008 | Jones et al. | 530/351 |
| 2004/0002474 | A1 | 1/2004 | Heinrichs et al. | 514/44 |
| 2004/0132977 | A1 | 7/2004 | Gantier et al. | 530/351 |
| 2004/0230040 | A1 | 11/2004 | Cox, III | 530/351 |

FOREIGN PATENT DOCUMENTS

| WO | WO 93/04699 A1 | 3/1993 |
|---|---|---|
| WO | WO 97/12630 A1 | 4/1997 |
| WO | WO 01/54678 A2 | 8/2001 |
| WO | WO 02/066649 A2 | 8/2002 |
| WO | WO 2004/022747 | 3/2004 |
| WO | WO 2004/089280 A2 | 10/2004 |
| WO | WO 2005/016371 | 2/2005 |
| WO | WO 2006/020580 | 2/2006 |

OTHER PUBLICATIONS

International Search Report corresponding to PCT/IL06/00754, filed Jun. 28, 2006.*
Argos, "A possible homology between immunodeficiency virus p24 core protein and picornaviral VP2 coat protein: prediction of HIV p24 antigenic sites," The EMBO Journal, 8(3): 779-785 (1989).
Chawla-Sarkar et al., "Preferential Induction of Apoptosis by Interferon (IFN)-β Compared with IFN-α2: Correlation with TRAIL/Apo2L Induction in Melanoma Cell Lines," Clinical Cancer Research, 7: 1821-1831 (2001).
Gilli et al., "Neutralizing antibodies against IFN-β in multiple sclerosis: antagonization of IFN-β mediated suppression of MMPs," Brain, 127: 259-268 (2004).
Hu et al., "Human IFN-α Protein Engineering: The Amino Acid Residues at Positions 86 and 90 are Important for Antiproliferative Activity," The Journal of Immunology, 167: 1482-1489 (2001).
Jaitin et al., "Inquiring into the Differential Action of Interferons (IFNs): an IFN-α2 Mutant with Enhanced Affinity to IFNAR1 is Functionally Similar to IFN-β," Molecular and Cellular Biology, 26(5): 1888-1897 (2006).
Kalie et al., "An Interferon α2 Mutant Optimized by Phage Display for IFNAR1 Binding Confers Specifically Enhanced Antitumor Activities," The Journal of Biological Chemistry, 282(15): 11602-11611 (2007).
Lamken et al., "Ligand-induced Assembling of the Type 1 Interferon Receptor on Supported Lipid Bilayers," J. Mol. Biol., 341: 303-318 (2004).
Piehler et al., "Biophysical Analysis of the Interaction of Human Ifnar2 Expressed in *E. coli* with IFNα2," J. Mol. Biol., 289: 57-67 (1999).
Piehler et al., "Mutational and Structural Analysis of the Binding Interface between Type 1 Interferons and their Receptor Ifnar2," J. Mol. Biol., 294: 223-237 (1999).
Riss et al., "Use of Multiple Assay Endpoints to Investigate the Effects of Incubation Time, Dose of Toxin, and Plating Density in Cell-Based Cytotoxicity Assays," Assay and Drug Development Technologies, 2(1): 51-62 (2004).
Tsutsumi et al., "Site-specific chemical modification with polyethylene glycol of recombinant immunotoxin anti-Tac(Fv)-PE38 (LMB-2) improves antitumor activity and reduces animal toxicity and immunogenicity," PNAS, 97(15): 8548-8553 (2000).

(Continued)

*Primary Examiner*—Robert Landsman
*Assistant Examiner*—Bruce D Hissong
(74) *Attorney, Agent, or Firm*—Winston & Strawn LLP

(57) ABSTRACT

The present invention provides IFNα2 mutants and active fragments, analogs, derivatives, and variants thereof that have improved specific agonist or antagonist activity as compared to wild-type IFNα2. The present invention further provides pharmaceutical compositions comprising IFNα2 mutants useful for treating or preventing cancer, autoimmune diseases, infectious diseases or disorders associated with increased expression of IFNα2.

7 Claims, 7 Drawing Sheets

OTHER PUBLICATIONS

Zafranskaya et al., "Interferon-β therapy reduces CD4+ and CD8+ T-cell reactivity in multiple sclerosis," Immunology, 121: 29-39 (2006).

U.S. Appl. No. 11/969,319 Requirement for Restriction/Election dated Apr. 21, 2009.

U.S. Appl. No. 11/969,319 Non-Final Rejection dated Sep. 4, 2009.

Arduini, Robert M. et al., "Characterization of a Soluble Ternary Complex Formed Between Human Interferon-β-1a and its Receptor Chains", Protein Science, vol. 8, pp. 1867-1877 (1999).

Brierley, Melissa M. et al., "IFN-α/β Receptor Interactions to Biologic Outcomes: Understanding the Circuitry", Journal of Interferon and Cytokine Research, vol. 22, pp. 835-845 (2002).

Campbell, Iain L. et al., "Essential Role for Interferon-γ and Interleukin-6 in Autoimmune Insulin-dependent Diabetes in NOD/Wehi Mice", Journal of Clin. Invest., vol. 87, pp. 739-742 (1991).

Chill, Jordan H., et al., "The Human Type I Interferon Receptor: NMR Structure Reveals the Moleculor Basis of Ligand Binding", Structure, vol. 11, pp. 791-802 (2003).

Cutrone, Elizabeth C. et al., "Identification of Critical Residues in Bovine IFNAR-1 Responsible for Interferon Binding", Journal of Biological Chemistry, vol. 276, pp. 17140-17148 (2001).

de Veer, Michael J. et al., "Functional Classification of Interferon-Stimulated Genes Identified Using Microarrays", Journal of Leukocyte Biology, vol. 69, pp. 912-920 (2001).

Der, Sandy D. et al., "Identification of Genes Differentially Regulated by Interferon α, β, or γ Using Oligonucleotide Arrays", Proc. National Academy Sci. USA, vol. 95, pp. 15623-15628 (1998).

Evinger, Marian et al., Antiproliferative and Antiviral Activities of Human Leukocyte Interferons, Archives of Biochemistry and Biophysics, vol. 210, pp. 319-329 (1981).

Fernandez-Martin, A. et al, "VIP Prevents Experimental Multiple Sclerosis by Downregulating Both Inflammatory and Autoimmune Components of the Disease", Ann. N.Y. Academy of Science, vol. 1070, pp. 276-281 (2006).

Gavutis M. et al., "Lateral Ligand-Receptor Interactions on Membranes Probed by Simultaneous Fluorescence-Interference Detection", Biophysical Journal, vol. 88, No. 6, pp. 4289-4302 (2005).

Goldman, Lisa A. et al., "Mapping Human Interferon-alpha (IFN-α2) Binding Determinants of the Type I Interferon Receptor Subunit IFNAR-1 with Human/Bovine IFNAR-1 Chimeras", Biochemistry Journal, vol. 37, pp. 13003-13010 (1998).

Hu, Renqiu et al., "Divergence of Binding, Signaling, and Biological Responses to Recombinant Human Hybrid IFN", Journal of Immunology, vol. 163, pp. 854-860 (1999).

Klaus, Werner et al., "The Three-Dimensional High Resolution Structure of Human Interferon α-2a Determined by Heteronuclear NMR Spectroscopy in Solution", Journal of Molecular Biology, vol. 274, pp. 661-675 (1997).

Kotenko, Sergei V. et al., "Full House: 12 Receptors for 27 Cytokines", International Immunopharmacology, vol. 4, pp. 593-608 (2004).

Piehler, Jacob et al., "Fast Transient Cytokine-Receptor Interactions Monitored in Real Time by Reflectometric Interference Spectroscopy", Analytical Biochemistry, vol. 289, pp. 173-186 (2001).

Piehler, Jacob et al., "New Structural and Functional Aspects of the Type I Interferon-Receptor Interaction Revealed by Comprehensive Mutational Analysis of the Binding Interface", Journal of Biological Chemistry, vol. 275, No. 51, pp. 40425-40433 (2000).

Platanias, Leonidas C. et al., "Signaling Pathways Activated by Interferons", Experimental Hematology, vol. 27, pp. 1583-1592 (1999).

Roisman, Laila C. et al., "Mutational Analysis of the IFNAR1 Binding Site on IFNα2 Reveals the Architecture of a Weak Ligand-Receptor Binding-Site", Journal of Molecular Biology, vol. 353, pp. 271-281 (2005).

Runkel, Laura et al., "Systematic Mutational Mapping of Sites on Human Interferon-B-1a that are Important for Receptor Binding and Functional Activity", Biochemistry, vol. 39, pp. 2538-2551 (2000).

Schmeisser, Hana et al., "Amino Acid Substitutions in Loop BC and Helix C Affect Antigenic Properties of Helix D in Hybrid IFN-α21a/α2c Molecules", Journal of Interferon and Cytokine Research, vol. 22, pp. 463-472 (2002).

Schmitt, Hans-Martin, et al., "An Integrated System for Optical Biomolecular Interaction Analysis", Biosensors & Bioelectronics, vol. 12, No. 8, pp. 809-816 (1997).

Uzé, Gilles et al., Genetic Transfer of a Functional Human Interferon Alpha Receptor into Mouse Cells: Cloning and Expression of its cDNA. Cell., vol. 60, pp. 225-234 (1990).

Villa Erica et al., 1996, "Alpha but not Beta Interferon is Useful in Chronic Active Hepatitis due to Hepatitis C Virus. A Prospective, Double-Blind, Randomized Study", Digestive Diseases and Sciences, vol. 41, No. 6, ppl. 1241-1247 (1996).

Ytterberg Steven R. et al., "Serum Interferon Levels in Patients with Systemic Lupus Erythematosus", Arthritis and Rheumatism, vol. 25, pp. 401-406 (1982).

* cited by examiner

Fig. 2

```
Receptor                   2      22  22222
                           -          -----
IFNα2    1  --CDLPQTHSLGSRRTLMLLAQMR-KISLFSCLKDRHDFGFPQEEF-GNQFQKAETIPVL
IFNα5    1  --...........H...M........-R..............R......D........A.S..
IFNα13   1  --....E....DN.........S-R..PS...M.............D........PA.S..
IFNα1    1  --........N..A.I.....G-R.PP..................D........QA.S..
IFNα21   1  --........N..A.I.....G-R..P...................D........QA.S..
IFNα4    1  --........N..A.I.....G-R..H................E...D.H....TQA.S..
IFNα7    1  --......RN..A.I.....G-R..P........E.R..E...D.H....TQA.S..
IFNα10   1  --........N..A.I..G..G-R..P..........RI.....D........QA.S..
IFNα14   1  --.N.S.....NN......M....-R..P............E......D........QA.S..
IFNα16   1  --........N..A.I.....G-R..H.........Y.......V.D........QA.SAF
IFNα8    1  --........N..A.I.....-R..P................E.....DDK.....QA.S..
IFNω     1  --.....N.G.L..N..V..H...-R..P.L.....R..R....MVK.S.L...HVMS..
IFNβ     1  SYNL.GFLQRSSNFQCQK...W.LNGRLEY--......MN.DI.E.IKQLQ....EDAALTI Receptor   11   1  11   1              1        1    1
           ++   +  --   -              -        -    -
IFNα2   57 HEMIQQIFNLFSTKDSSAAWDETLLDKFYTELYQQLNDLEACVIQGVGVTETPLMKEDSI
IFNα5   58 ..V...T.......V....R....L...........M.E.W.GG....N....
IFNα13  58 ..L.........T.........D.....C...........M.EER.G.....NA...
IFNαI   58 .....T.......T.EQS..E..S...N............E...E.....NV...
IFNα21  58 .....T.......T.EQS..E..S...N....M.......E...E.....NV...
IFNα4   58 .....T.......E....EQS..E..S...............E...E.....NV...
IFNα7   58 .....T.......E....EQS..E..S...............E...E.....N..F.
IFNα10  58 .....T.......E....EQS..E..S...............E...E.....N....
IFNα14  58 ..M..T.......N..........E...I..F..M........E...E.....N....
IFNα16  58 .....T....................I..F........T.E...E.IA..N....
IFNα8   58 .....T...........L......E..I..D......S..M.E...I.S...Y....
IFNω    58 ...L....S..H.ER.....NM....QLH.G.H...QH..T.LL.V..EG.SAGAISSPA
IFNβ    59 Y..L.N...AI.RQDS..TG.N...IVENLLANV.H.I.H.KTVLEEKLEKEDFTRG.LM.S Receptor                 2           2 222   22
                         -            - --   --
117 LAVRKYFQRITLYLKEKKYSPCAWEVVRAEIMRSFSLSTNLQESLRSKE------ (SEQ ID NO:2)
118 ................T........................S.R....R..R..------ (SEQ ID NO:36)
118 ...K...R........T........................L........R..R..------ (SEQ ID NO:37)
118 ...K............T........................KIF..R..R..------ (SEQ ID NO:1)
118 ...K............T........................KIF..R..R...Z----- (SEQ ID NO:38)
118 ................T........................L.F.....KR..R.D------ (SEQ ID NO:39)
118 ................M..........................F............... (SEQ ID NO:40)
118 .............I.R..........................L.F.....KR..R..------ (SEQ ID NO:41)
118 ...K............M..........................F.....KR..R..------ (SEQ ID NO:42)
118 ................MG.........................F.....KG..R.------ (SEQ ID NO:43)
118 ................T.....S....................I..KR.K..------ (SEQ ID NO:44)
118 .TL.R...G.RV........D.......M...K.LF....M..R....DRDLGSS (SEQ ID NO:45)
119 .HLKR.YG..LH...A.E..H...TI..V..L.N.YFINR.TGY...N-------- (SEQ ID NO:3)
```

NUCLEIC ACID MOLECULES ENCODING RECOMBINANT INTERFERON-α2 (IFNα2) MUTANTS

This application is a 371 filing of International Patent Application PCT/IL2006/754, filed Jun. 28, 2006, which claims the benefit of application no. 60/694,810 filed Jun. 29, 2005, the entire content of each of which is expressly incorporated herein by reference thereto.

FIELD OF THE INVENTION

The present invention relates to recombinant interferon α2 (IFNα2) mutants, fragments, analogs, derivatives, and variants thereof, having improved specific agonist or antagonist activity compared to wild-type IFNα2, and to pharmaceutical compositions thereof, useful for treating or preventing cancer, autoimmune diseases, infectious diseases and disorders associated with increased expression of IFNα2.

BACKGROUND OF THE INVENTION

Interferons (IFNs) were discovered in 1957 by Isaacs and Lindenmann, and were named for their ability to interfere with viral proliferation. Interferons can also combat bacterial and parasitic infections, inhibit cell division, inhibit spontaneous apoptosis, and promote or impede the differentiation of cells. Based on their receptor specificity, two types of interferons are recognized: Type I and Type II. The Type I interferons are a family of monomeric proteins including IFNα and IFNω that are products of leukocytes, IFNβ that is produced by fibroblasts, and IFNτ that has been described only in ungulate species.

The only known type II interferon the dimeric IFNγ, which is produced exclusively by lymphocytes. The interferon alpha family is composed of 13 intronless fully translated genes (excluding pseudogenes). Each member includes mature proteins of 165 or 166 amino acid residues, with two conserved disulfide bonds: Cys1-Cys98 and Cys29-Cys138. A high level of sequence homology (80%) is displayed among the various interferon alpha sub-types, and about 35% homology exists between these sub-types and the IFNβ. In spite of the high homology of the different sub-types, their biological activities, among them antiproliferative, antiviral, and immunomodulation, differ notably.

The structure of several type I interferons have been solved including murine IFNβ (1IFA, 1RMI), human IFNβ (1AU1), human IFNα2 (1RH2, 1ITF), and ovine IFNτ (1B5L). Structurally, interferons are members of the α-helical cytokine family. All the type I interferons signal through a common receptor complex composed of IFNAR1 and IFNAR2. The major ligand-binding component of the type I interferon receptor is IFNAR2, with a binding affinity of ~10 nM for IFNα2. The structure of the extracellular part of IFNAR2 consists of two immunoglobulin-like domains, with the binding site of IFNα2 being located at the N-terminal domain and the connecting loop.

Mature IFNAR1 is a 530 amino acid protein, with a transmembrane segment composed of 21 residues, and a cytoplasmatic domain of 100 residues. The structure of the extracellular part of IFNAR1 is unknown, but from the sequence one can deduce that it is composed of four immunoglobulin-like domains. Binding of IFNα2 to IFNAR1 is weak, with the affinity measured on an artificial membrane being 1.5-5 µM. Bovine IFNAR1 (BoIFNAR1) and the human IFNAR1 (HuIFNAR1), are 68% identical. The sub-domains 2 and 3 of HuIFNAR1 have been shown to play a critical role in binding to IFNα2. By exchanging these sub-domains with homologous BoIFNAR1, the affinity was increased substantially. The soluble BoIFNAR1 can bind human interferons with a 10 nM affinity, which is 500-fold greater than that of HuIFNAR1. Murine cells expressing IFNAR2 bind IFNα2 with an affinity of 8 nM, whereas cells expressing only IFNAR1 exhibit no ligand binding. Upon co-expression of IFNAR1 and IFNAR2, a ten-fold increase in the affinity for IFNα2 was observed. Using in-vitro studies on artificial membranes it was shown that the magnitude of IFNAR1-induced increase in binding affinity of the ternary complex relates to the relative surface concentration of this receptor. The location of the IFNAR1 binding site on interferon was mapped on IFNβ to be located on the B, C, and D helices and the DE loop while Ala scan mutagenesis of IFNα2 have suggested that the IFNAR1 binding site is restricted to helices B and C.

A number of studies have suggested that the formation of the ternary complex occurs in a sequential mode, beginning with interferon binding IFNAR2 to form an intermediate complex, and followed by the recruitment of IFNAR1. The IFNAR1-IFNβ-IFNAR2 complex has been shown to have a 1:1:1 stoichiometry. The IFNAR1 receptor is an essential component of the interferon receptor complex, with an IFNAR1 null mutation, or the addition of neutralizing Ab against this receptor resulting in a complete lack of the antiviral and antiproliferative responses to IFNα and IFNβ. Association of IFNAR1 and IFNAR2, stimulates the activation of the constitutively-associated intracellular kinases Jak1 and Tyk2, leading to a tyrosine phosphorylation cascade that results in the dimerization of the phosphorylated signal transducers and activators of transcription (STATs), and transport into the nucleus, where they bind to specific DNA sequences and stimulate transcription of hundreds of responsive genes.

The question remains open on how very similar IFNs induce differential activities on the same cell type. It has been suggested that the biological activities of different IFNα subtypes correlate with their respective binding affinities and the cell type used.

The vertebrate type I interferons are recognized by a single shared receptor, composed of two transmembrane proteins (IFNAR1 and IFNAR2), present their activity through their associated Jak kinases with the Stat transcription factors as their main targets (Brierley, M. M. & Fish, E. N. 2002. *J Interferon Cytokine Res.* 22, 835-845). Typically recognized by the IgG-like folds of their extracellular domains (hCR domains), IFNAR2 and IFNAR1 are regarded respectively as binding proteins and accessory transducing factors—i.e., the alpha and beta chains of heteromeric receptors. A difference in ligand dissociation constants of the two chains is implicit in the definition. Nevertheless, both contribute to the creation of high affinity binding sites. The combination of a "common" beta chain with different recognition chains is a feature of heteromeric receptors that respond differentially to different ligands. The ability to interact with different alpha-chains establishes potential network connections for differential receptor expression (Kotenko, S. V. & Langer, J. A. 2004. *Int Immunopharmacol* 4, 593-608). When, like IFNAR1, they possess the capacity of interacting with elements of different signaling pathways, they may establish connections for differential gene expression (Platanias, L. C. & Fish, E. N. 1999. *Experimental Hematology* 27, 1583-1592).

The human IFNs number 12 distinct non-allelic alpha proteins, one beta and one omega. As expected from a family with marked sequence homology, a shared 3D core structure and a shared receptor, the activities of the Type I IFNs overlap. Nevertheless they can be recognized and even classified by their amino acid differences and numerous instances of relative differences in activity have been noted. The emerging picture is that functional differences appear only in specific physiological contexts. In addition of their local action in conferring antiviral protection on almost any cell, they are linked to the development of second line antiviral defenses. It was noted that a possible difference between the IFNs might be their potential to bind tightly to IFNAR1 (Roisman et al., 2005. *J Mol. Biol.* 353, 271-281).

The differential activities of Type I IFNs have been a subject of intense investigations over many years. Particularly it was noted that IFNβ has an additional repertoire of activities over IFNα. Detailed analysis of the differences between these two IFNs has shown that IFNβ has a general higher activity in transcription activation of IFN responsive genes, and is active at reduced IFN levels. Binding studies suggested that affinity towards the accessory subunit IFNAR1 is the key differences between IFNα2 and IFNβ (Jaitin, 2006. *Mol Cell Biol.* 26, 1888-1897).

IFNα2 is known to have anti-cancer effects. However, this treatment is not always effective and sometimes results in intolerable side effects related to the dosage and duration of therapy. WO 97/12630 discloses treating cancer patients with temozolomide in combination with IFNα2. WO 01/54678 discloses treating cancer patients with temozolomide and pegylated interferon.

Hepatitis C virus (HCV) infection is the most common chronic blood borne infection in the United States. Although the numbers of new infections have declined, the burden of chronic infection is substantial; the Center for Disease Control estimates 3.9 million (1.8%) infected persons in the United States. Chronic liver disease is the tenth leading cause of death among adults in the United States, and accounts for approximately 25,000 deaths annually, or approximately 1% of all deaths. Studies indicate that 40% of chronic liver disease is HCV-related, resulting in an estimated 8,000-10,000 deaths each year. HCV-associated end-stage liver disease is the most frequent indication for liver transplantation among adults.

Antiviral therapy of chronic hepatitis C has evolved rapidly over the last decade, with significant improvements seen in the efficacy of treatment. Nevertheless, even with combination therapy using pegylated IFN-α plus ribavirin, 40% to 50% of patients fail therapy, i.e., are non-responders or relapsers. These patients currently have no effective therapeutic alternative. In particular, patients who have advanced fibrosis or cirrhosis on liver biopsy are at significant risk of developing complications of advanced liver disease, including ascites, jaundice, variceal bleeding, encephalopathy, and progressive liver failure, as well as a markedly increased risk of hepatocellular carcinoma.

Multiple sclerosis (MS) is a chronic, neurological, autoimmune, demyelinating disease. MS can cause blurred vision, unilateral vision loss (optic neuritis), loss of balance, poor coordination, slurred speech, tremors, numbness, extreme fatigue, changes in intellectual function (such as memory and concentration), muscular weakness, paresthesias, and blindness. Many subjects develop chronic progressive disabilities, but long periods of clinical stability may interrupt periods of deterioration. Neurological deficits may be permanent or evanescent. The pathology of MS is characterized by an abnormal immune response directed against the central nervous system. In particular, T-lymphocytes are activated against the myelin sheath of the central nervous system causing demyelination. In the demyelination process, myelin is destroyed and replaced by scars of hardened "sclerotic" tissue which is known as plaque. These lesions appear in scattered locations throughout the brain, optic nerve, and spinal cord. The two types of interferon-beta that are approved in the United States for use in treating MS are interferon-beta 1a and interferon-beta 1b.

Type I diabetes, also known as autoimmune diabetes or insulin-dependent diabetes mellitus (IDDM), is an autoimmune disease characterized by the selective destruction of pancreaticss cells by autoreactive T lymphocytes (Bach, 1994, Endocr. Rev. 15:516-542). The pathology of IDDM is very complex involving an interaction between an epigenetic event (possibly a viral infection), the pancreatic islet cells and the immune system in a genetically susceptible host. A number of cytokines, including IFN-α and IFN-γ, have been implicated in the pathogenesis of IDDM in humans and in animal models of the disease (Campbell et al., 1991, J. Clin. Invest. 87:739-742). It appears that local expression of IFN-α by pancreatic islet cells in response to potential diabetogenic stimuli such as viruses may trigger the insulitic process.

WO9304699 discloses a method for treatment of insulin dependent diabetes mellitus comprising administering an IFN-α antagonist.

Based on the increased level of IFN-α expression in patients with systemic lupus erythematosus (SLE), IFN-α has also been implicated in the pathogenesis of SLE (Ytterberg and Schnitzer, 1982, Arthritis Rheum. 25: 401-406). WO02066649 discloses anti-IFN-α specific antibodies for the treatment of insulin-dependent diabetes mellitus (IDDM) and systemic lupus elythematosus (SLE).

US Patent Application Publication No. 20040230040 discloses cysteine variants of α interferon-2. US Patent Application Publication No. 20040002474 discloses α interferon homologues having antiproliferative activity in a human Daudi cell line-based assay.

U.S. Pat. No. 4,588,585 discloses mutated IFN-β-1b in which Cys17 is changed to Ser17 via a T to A transition in the first base of codon 17, which prevents incorrect disulfide bond formation. WO2005016371 discloses a pharmaceutical composition comprising an improved recombinant human IFN-β-1b variant with a greater specific activity.

The available treatments for cancer, infectious diseases, multiple sclerosis, and autoimmune disorders associated with increased expression of IFNα2 are expensive, effective only in a certain percentage of patients and adverse side effects are not uncommon. There remains an unmet medical need for suitable therapeutic methods that are safe, reliable, efficacious, and cost effective.

SUMMARY OF THE INVENTION

The present invention provides novel IFNα2 mutants having important therapeutic utility. The variants of the invention have improved specificity as agonists or antagonists compared to wild-type IFNα2.

The present invention for the first time discloses the finding that a recombinant IFNα2 mutant mimics the binding properties of IFNβ (SEQ ID NO: 3) and shows key characteristics of differential IFNβ activity. This includes increased antiproliferative activity in vitro and in vivo, and specific down-regulation of the IFNAR2 receptor.

According to a first aspect, the present invention provides a recombinant interferon α2 (IFNα2) polypeptide, active fragment, analog, derivative and variant thereof, wherein said polypeptide comprises a mutation selected from at least one amino acid substitution within amino acid residues 57-89, and at least one amino acid substitution of the C terminal amino acid residues 159-165, as well as combinations thereof, wherein said polypeptide has improved specific agonist or antagonist activity, as compared to wild-type IFNα2 (SEQ ID NO: 2).

According to some embodiments the polypeptide comprises at least one mutation selected from the group consisting of H57A (SEQ ID NO: 24), E58A (SEQ ID NO: 25), Q61A (SEQ ID NO: 26), H57Y (SEQ ID NO: 27), E58N (SEQ ID NO: 28), Q61S (SEQ ID NO: 29), and combinations thereof, wherein said polypeptide has improved specific agonist or antagonist activity, as compared to wild-type IFNα2 (SEQ ID NO: 2).

According to one embodiment, the present invention provides a triple mutant H57A, E58A, Q61A (SEQ ID NO: 5) having improved specific activity as compared to wild-type IFNα2 (SEQ ID NO: 2).

According to another embodiment, the present invention provides a quadruple mutant N65A, L80A, Y85A, Y89A (SEQ ID NO: 6) having antagonist activity as compared to wild-type IFNα2.

According to a further embodiment, the present invention provides an IFNα2 protein comprising a substitution of the C terminal ESLRSKE to KRLKSKE (SEQ ID NO: 7) having improved specific activity as compared to wild-type IFNα2.

The specific mutations of the IFNα2 mutants of the invention are each located at a different position on the protein, and therefore can be combined to yield additional, or increased effects.

According to one embodiment, the present invention provides an IFNα2 variant comprising a combination of the triple mutant H57A, E58A, Q61A and the substitution of the C terminal of ESLRSKE to KRLKSKE (SEQ ID NO: 8), with very high specific activity.

According to another embodiment, the present invention provides an IFNα2 variant comprising a combination of the quadruple mutant N65A, L80A, Y85A, Y89A and the substitution of the C terminal of ESLRSKE to KRLKSKE (SEQ ID NO: 9), with an increased binding affinity to IFNAR2, but with very low biological activity. This IFNα2 variant is now disclosed to act as an IFN antagonist, which blocks the natural activity of IFNs through their receptors.

According to a further embodiment, the present invention provides a triple mutant H57M, E58D, Q61L (SEQ ID NO: 10) having improved specific activity as compared to wild-type IFNα2 (SEQ ID NO: 2).

According to yet another embodiment, the present invention provides a triple mutant H57Y, E58N, Q61S (SEQ ID NO: 11) having improved specific activity as compared to wild-type IFNα2 (SEQ ID NO: 2).

According to still another embodiment, the present invention provides an IFNα2 variant comprising a combination of the triple mutant H57M, E58D, Q61L and the substitution of the C terminal of ESLRSKE to KRLKSKE (SEQ ID NO: 12) having improved specific activity as compared to wild-type IFNα2 (SEQ ID NO: 2).

According to still a further embodiment, the present invention provides an IFNα2 variant comprising a combination of the triple mutant H57Y, E58N, Q61S and the substitution of the C terminal of ESLRSKE to KRLKSKE (SEQ ID NO: 13) having improved specific activity as compared to wild-type IFNα2 (SEQ ID NO: 2).

According to some embodiments, the present invention provides PEGylated IFNα2 mutants with increased specific activity.

According to another aspect, the present invention provides DNA molecules encoding the polypeptides of the invention. According to one embodiment, the DNA molecules comprise a sequence selected from SEQ ID NOS: 15-23 SEQ ID NOS: 30-35.

According to an additional aspect, the present invention provides a vector comprising a DNA molecule of the invention, wherein the vector is capable of expressing a mutant IFNα2 polypeptide in a prokaryotic host cell or eukaryotic host cell.

According to yet another aspect, the present invention provides a host cell comprising a vector of the invention.

According to another aspect, the present invention provides a pharmaceutical composition comprising as an active ingredient a recombinant interferon α2 (IFNα2) polypeptide, active fragment, analog, derivative and variant thereof, wherein said polypeptide comprises a mutation selected from at least one amino acid substitution within amino acid residues 57-89, at least one amino acid substitution of the C terminal amino acid residues 159-165, as well as combinations thereof, wherein said polypeptide has improved specific agonist or antagonist activity, as compared to wild-type IFNα2 (SEQ ID NO: 2), further comprising a pharmaceutically acceptable carrier.

According to some embodiments, the pharmaceutical composition comprising recombinant interferon α2 (IFNα2) polypeptide, having any one of SEQ ID NOS: 5-13 and SEQ ID NOS: 24-29, fragments, analogs, derivatives and variants thereof.

According to one embodiment, said pharmaceutical composition comprising recombinant interferon α2 (IFNα2) polypeptide having any one of SEQ ID NOS: 5, 7, 8, 10, 11, 12 and 13, fragments, analogs, derivatives and variants thereof, wherein said polypeptide has improved specific agonist activity.

According to another embodiment, the pharmaceutical composition comprising recombinant interferon α2 (IFNα2) polypeptide having any one of SEQ ID NOS: 6 and 9, fragments, analogs, derivatives and variants thereof, wherein said polypeptide has improved specific antagonist activity.

According to a further aspect, the present invention provides a method of treating or preventing a disorder or disease associated with modulation of IFN comprising administering to a subject in need thereof a therapeutically effective amount of the pharmaceutical composition of the invention, wherein said disorder or disease is selected from the group consisting of cancer, autoimmune disease and infectious disease.

According to one embodiment, said autoimmune disease is multiple sclerosis (MS). According to a preferred embodiment, said MS is selected from the group consisting of relapsing remitting MS, secondary progressive MS, primary progressive MS, and progressive relapsing MS.

According to some embodiments, the IFNα2 mutants having any one of SEQ ID NOS: 5, 7, 8, 10, 11, 12 and 13 are useful for treating or preventing MS.

According to one embodiment said cancer is selected from the group consisting of hairy cell leukemia, Kaposi's sarcoma, multiple myeloma, chronic myelogenous leukemia, non-Hodgkins's lymphoma and melanoma.

According to another embodiment, the present invention provides a method of inhibiting the growth of cancer cells, comprising exposing cancerous cells to a therapeutically effective amount of an IFNα2 mutant having any one of SEQ ID NOS: 5, 7, 8, 10, 11, 12 and 13, fragments, analogs, and derivatives thereof.

According to one embodiment said infectious disease is hepatitis virus infection.

According to some embodiments said hepatitis is selected from the group consisting of hepatitis A, hepatitis B and hepatitis C.

According to another embodiment, the IFNα2 mutants having any one of SEQ ID NOS: 5, 7, 8, 10, 11, 12 and 13 are useful for treating or preventing infectious hepatitis virus infection.

According to a further embodiment, the present invention discloses methods of treatment or prophylaxis of disorders associated with increased expression of IFNα2 including but not limited to insulin dependent diabetes mellitus (IDDM) and systemic lupus erythematosus (SLE) comprising administering to a subject in need thereof an IFN-α2 mutant having SEQ ID NOS: 6, and 9, fragments, analogs, and derivatives thereof.

According to still another aspect, the present invention provides the use of the IFNα2 mutants of the invention for the preparation of a medicament for the treatment or prevention of disorders or diseases associated with modulation of IFN.

These and other embodiments of the present invention will become apparent in conjunction with the figures, description and claims that follow.

BRIEF DESCRIPTION OF THE FIGURES

FIG. 1A shows binding curve for capturing IFNAR1 with immobilized mAb DB2, followed by cross-linking with mAb AA3. FIG. 1B shows steady state affinity analysis. Binding of IFNα2 E58A (thick gray) and E96A (thin black) at different concentrations between 0.25 and 4 μM (see numbers in figure), to IFNAR1 immobilized on the surface. FIG. 1C shows the dissociation reaction of IFNα2, IFNβ and the triple mutant H57A, E58A, Q61A (SEQ ID NO: 5) from surface-immobilized IFNAR1-EC followed in real-time. The rate of dissociation is directly related to the binding affinity, with the data summarized in Tables 1 and 3.

FIG. 2 shows mutant analysis of IFNAR1 and IFNAR2 binding to IFNα2. Type I interferons are aligned relative to IFNα2. Residues that are underlined are those which mutant to Ala did not change binding to either receptor. The "+" and "−" signs above symbolize whether the mutation caused an increase or decrease in binding affinity of IFNα2 upon mutation (see Table 1). The number above symbolize whether the change is due to binding to IFNAR1 (1) or IFNAR2 (2). The C-terminal residues on IFNα8 are in bold to mark the changes made in SEQ ID 7. The boxed residues are those relating to SEQ ID 5-13.

FIGS. 3A-3B show the functional epitope for binding IFNAR1 on IFNα2. FIG. 3A shows plot of the change in binding affinity of all the mutant proteins analyzed in by us to both IFNAR1 and IFNAR2. FIG. 3B shows a surface representation of a model of the complex of IFNα2 with IFNAR2 as determined previously. Residues that upon mutation change binding to IFNAR1 are given numbers. Residues that upon mutation increase the binding affinity by >2-fold are underlined (57, 58, 61). This picture was composed with PyMol.

FIG. 4A shows one set of raw data of the antiproliferative response upon administration of a serial dilution of interferon at a range of 250 nM-0.48 pM of IFNα2 and 125 nM-0.24 pM of IFNβ. FIGS. 4B and 4C show the densitometry readings for three independent antiproleferative (4B) and antiviral (4C) experiments including also the triple mutant H57A, E58A, Q61A (SEQ ID NO: 5). The data are of 6 repeats showing, including the standard error. The curve was fitted a dose response equation, and represents the best fit for the combined data.

FIG. 5A shows relative (to wt) antiviral activity plotted versus the relative antiproliferative activity of 21 IFNα2 single mutants, triple mutant H57A, E58A, Q61A (SEQ ID NO: 5), quadruple mutant N65A, L80A, Y85A, Y89A (SEQ ID NO: 6), (SEQ ID NO:7), the triple mutant H57Y, E58N, Q61S (SEQ ID NO: 11) and of IFNβ. FIG. 5B shows relative antiviral and antiproliferative activities of the same proteins plotted versus their relative binding affinity for IFNAR1-EC. All data are from Tables 1-4. The linear line represents a theoretical relationship between biological activity and affinity. Points above the line are for mutants were the change in biological activity (antiviral or antiproliferative) is weaker than their change in affinity, and points below the line are the opposite.

FIG. 6A shows relative (to no treatment) expression levels of the 395 genes plotted in ascending order according to fold-change. FIG. 6B shows the expression levels plotted relative to the expression levels upon addition of 0.15 nM IFNβ. The only exception is for expression level of the untreated control (black dots), which is plotted against a second set of control to evaluate the random level of fluctuation. FIG. 6C shows cluster analysis of the interferon-induced genes for the four treatments. The gene expression profiles of IFNβ and HEQ (SEQ ID NO: 5) cluster together, with a very short distance between them. The expression profile of cells treated with 3 nM IFNα2-wt clusters next, while the gene-expression profile of 0.3 nM IFNα2-wt is farther away.

DETAILED DESCRIPTION OF THE INVENTION

Figure 1:
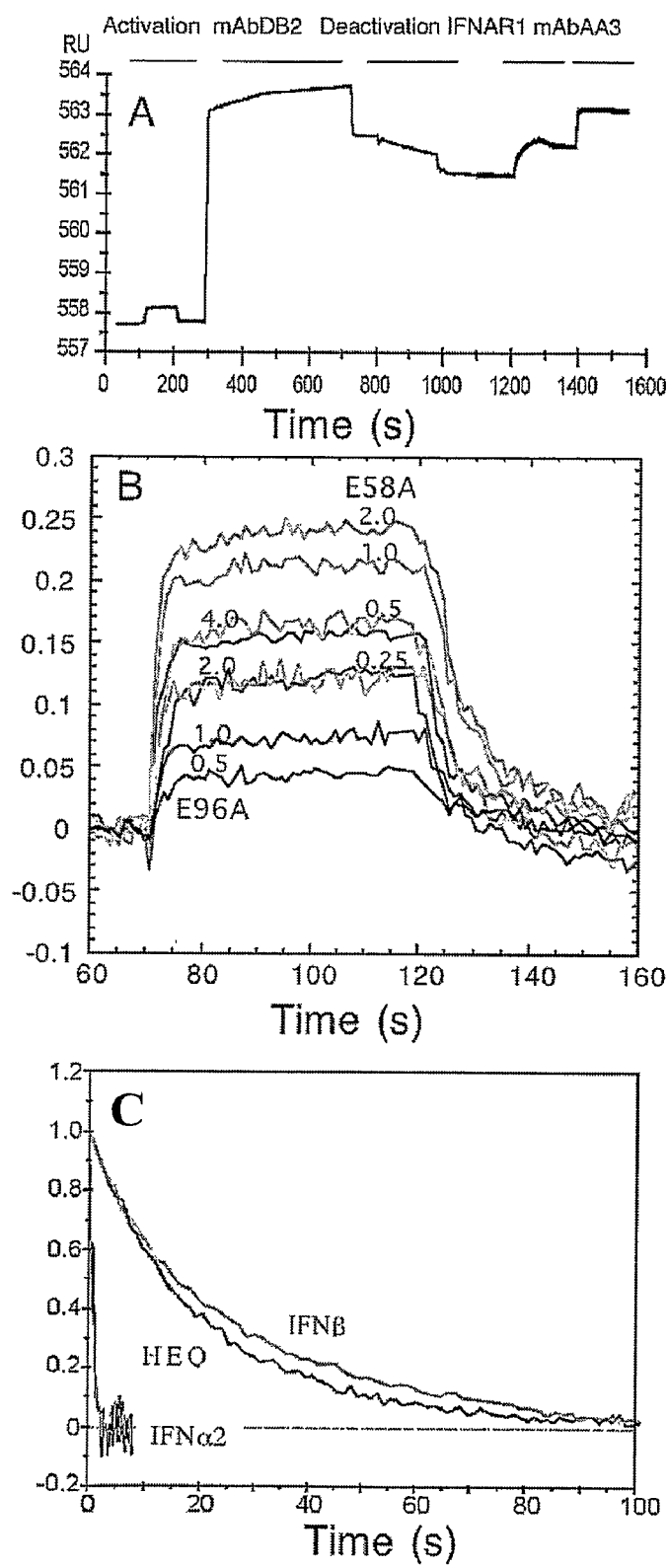
FIGS. 1A-1C show immobilization of type I Interferon receptor-extracellular domain (IFNAR1-EC) by affinity capturing and binding of IFNα2.

The present invention provides IFNα2 mutants and active fragments, analogs, derivatives, and variants thereof that have improved agonist or antagonist activity as compared to wild-type IFNα2 (SEQ ID NO: 2). The mutants of the invention provide improved therapeutic utility that may include at least one advantage selected from improved specificity or selectivity, improved duration of action, improved stability and fewer adverse effects.

The present invention further provides pharmaceutical compositions comprising IFNα2 mutants useful for treating or preventing cancer, multiple sclerosis, infectious diseases and disorders associated with increased expression of IFNα2 such as insulin dependent diabetes mellitus (IDDM) and systemic lupus erythematosus (SLE).

Definitions

The term interferon (IFN) or interferons (IFNs) refers to the family of secreted proteins, which are cytokines with antiviral, anti-protozoal, immunomodulatory, and cell growth regulatory activities. IFNs were originally classified by their sources: leukocytes IFN-α-1 (SEQ ID NO: 1), and IFN-α-2 (SEQ ID NO: 2), fibroblasts IFN-β (SEQ ID NO: 3), and immune cells IFN-γ (SEQ ID NO: 4). Particular note is made of IFNs alpha, beta, and gamma. Interferon alpha is the main type of interferon produced by the white blood cells.

The terms "analog", "fragment", "derivative", and "variant", when referring to the improved IFNα2 polypeptides of this invention means analogs, fragments, derivatives, and variants of such improved IFNα2 polypeptides that retain substantially similar functional activity or substantially the same biological function or activity as the improved IFNα2 polypeptides, as described herein.

An "analog" includes an improved IFNα2 polypeptide wherein at least one amino acid is substituted by another amino acid to produce an active analog of a polypeptide of the invention having increased activity, stability or longer half-life as compared to the polypeptides listed herein.

A "fragment" is a portion of an improved IFNα2 polypeptide of the present invention that retains substantially similar functional activity or substantially the same biological function or activity as an improved IFNα2 polypeptide, as shown in the in vitro assays disclosed herein, as described further below.

A "derivative" includes all modifications to an improved IFNα2 polypeptide of this invention that substantially preserve the functions disclosed herein and include additional structure and attendant function, e.g., PEGylated polypeptides, which have greater half-life.

A "variant" includes polypeptides having an amino acid sequence comprises a combination of the mutant IFNα2 polypeptides of this invention that retains substantially similar functional activity or an increased functional activity as compared to the original mutant IFNα2 polypeptides.

"Substantially similar functional activity" and "substantially the same biological function or activity" each means that the degree of biological activity is within about 50% to 100% or more, preferably within 80% to 100% or more, and more preferably within about 90% to 100% or more, of that biological activity demonstrated by the polypeptide to which it is being compared when the biological activity of each polypeptide is determined by the same procedure or assay.

"Similarity" between two polypeptides is determined by comparing the amino acid sequence of one polypeptide to the sequence of a second polypeptide. An amino acid of one polypeptide is similar to the corresponding amino acid of a second polypeptide if it is identical or a conservative amino acid substitution. Conservative substitutions include those described in Dayhoff, M. O., ed., The Atlas of Protein Sequence and Structure 5, National Biomedical Research Foundation, Washington, D.C. (1978), and in Argos, P. (1989) EMBO J. 8: 779-785. For example, amino acids belonging to one of the following groups represent conservative changes or substitutions: Ala: -Pro, Gly, Gln, Asn, Ser, Thr: -Cys, Ser, Tyr, Thr; -Val, Ile, Leu, Met, Ala, Phe; -Lys, Arg, His; -Phe, Tyr, Trp, His; and -Asp, Glu.

"Specific activity" as used herein with reference to an IFNα2 mutant of the present invention means a biological activity or function of an IFNα2. The biological activities or functions of IFNα2 are well known in the art and include, but are not limited to antiproliferative activity. Such specific activity can be detected and measured using the methods described herein or using any method known in the art.

"Improved specific activity" as used herein means that the specific activity or the antagonistic activity of the IFNα2 composition of the present invention is greater than that of a reference IFNα2 wild-type composition. The specific activity of an IFNα2 composition of the present invention can be assayed as compared to the specific activity of the reference IFNα2 wild-type composition, using a method for detecting and/or measuring an IFNα2 specific activity, e.g., as described herein or as known in the art.

"IFNα2 composition" refers to an IFNα2 polypeptide, fragment, analog, derivative, or variant thereof, or composition (e.g., a pharmaceutical composition) comprising an IFNα2 polypeptide, fragment, analog, derivative, or variant thereof.

The term "recombinant proteins or polypeptides" refer to proteins or polypeptides produced by recombinant DNA techniques, i.e., produced from cells, prokaryotic or eukaryotic, including e.g., microbial or mammalian, transformed by an exogenous recombinant DNA expression construct encoding the desired protein or polypeptide. Proteins or polypeptides expressed in most bacterial cultures will typically be free of glycan. Proteins or polypeptides expressed in yeast may have a glycosylation pattern different from that expressed in mammalian cells.

An "expression vector" as used herein refers to a nucleic acid molecule capable of replication and expressing a gene of interest when transformed, transfected or transduced into a host cell. The expression vectors comprise one or more phenotypic selectable markers and an origin of replication to ensure maintenance of the vector and to, if desired, provide amplification within the host. Selectable markers include, for example, sequences conferring antibiotic resistance markers, which may be used to obtain successful transformants by selection, such as ampicillin, tetracycline and kanamycin resistance sequences, or supply critical nutrients not available from complex media. Suitable expression vectors may be plasmids derived, for example, from pBR322 or various pUC plasmids, which are commercially available. Other expression vectors may be derived from bacteriophage, phagemid, or cosmid expression vectors, all of which are described in sections 1.12-1.20 of Sambrook et al., (Molecular Cloning: A Laboratory Manual. $3^{rd}$ edn., 2001, Cold Spring Harbor Laboratory Press). Isolated plasmids and DNA fragments are cleaved, tailored, and ligated together in a specific order to generate the desired vectors, as is well known in the art (see, for example, Sambrook et al., ibid).

The term "native", "naturally occurring" or "wild type" (wt) proteins or polypeptides refer to proteins or polypeptides recovered from a source occurring in nature. The term "native IFN" or "wild type IFN" would include native or wild type IFN and would include post-translational modifications of IFN, including, but not limited to, acetylation, carboxylation, glycosylation, phosphorylation, lipidation, acylation, and cleavage.

The term "recombinant expression vector or plasmid" is a replicable DNA vector or plasmid construct used either to amplify or to express DNA encoding the proteins or polypeptides of the present invention. An expression vector or plasmid contains DNA control sequences and a coding sequence. DNA control sequences include promoter sequences, ribosome binding sites, polyadenylation signals, transcription termination sequences, upstream regulatory domains, and enhancers. Recombinant expression systems as defined herein will express the proteins or polypeptides of the invention upon induction of the regulatory elements.

The term "transformed host cells" refers to cells that have been transformed and transfected with exogenous DNA. Exogenous DNA may or may not be integrated (i.e., covalently linked) to chromosomal DNA making up the genome of the host cell. In prokaryotes and yeast, for example, the exogenous DNA may be maintained on an episomal element, such as a plasmid, or stably integrated into chromosomal DNA. With respect to eukaryotic cells, a stably transformed cell is one which is the exogenous DNA has become integrated into the chromosome. This stability is demonstrated by the ability of the eukaryotic cell lines or clones to produce via replication a population of daughter cells containing the exogenous DNA.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent.

"Therapeutical effective amount" refers to that amount of an improved IFNα2 polypeptide of the invention which, when administered to a subject in need thereof, is sufficient to effect treatment of the condition or disorder. For example for relapsing remitting multiple sclerosis (MS), cancer, infectious diseases or disorders associated with increased expression of IFNα2 such as insulin dependent diabetes mellitus (IDDM) and systemic lupus erythematosus (SLE).

The term "subject" refers to human subjects and non-human subjects.

The term "cancer" is meant to include all types of cancerous growths or oncogenic processes, metastatic tissues or malignantly transformed cells, tissues, or organs, irrespective of histopathologic type or stage of invasiveness. Examples of cancers include but are nor limited to solid tumors and leukemias, including: apudoma, choristoma, branchioma, malignant carcinoid syndrome, carcinoid heart disease, carcinoma (e.g., Walker, basal cell, basosquamous, Brown-Pearce, ductal, Ehrlich tumor, non-small cell lung, oat cell, papillary, bronchiolar, bronchogenic, squamous cell, and transitional cell), histiocytic disorders, leukemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adeno-carcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma, phyllodes, fibrosarcoma, hemangiosarcoma, leimyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neurofibromatosis, and cervical dysplasia, and other conditions in which cells have become immortalized or transformed.

"Treating MS" as used herein covers the treatment of disease-state in a subject, which disease-state is characterized by symptoms associated with MS, such as weakness, numbness, tremor, loss of vision, pain, paralysis, loss of balance, bladder and bowel dysfunction, and cognitive changes (primary symptoms); repeated urinary tract infections, disuse weakness, poor postural alignment and trunk control, muscle imbalance, decreased bone density, shallow, inefficient breathing, and bedsores (secondary symptoms); and depression (tertiary symptoms), and includes: (i) inhibiting the condition, i.e., arresting its development; or (ii) relieving the condition, i.e., causing regression of the condition.

The term "hepatitis virus infection" refers to infection with one or more of hepatitis A, B, C, D, or E virus, with blood-borne hepatitis viral infection being of particular interest.

As used herein, the term "hepatic fibrosis," used interchangeably herein with "liver fibrosis," refers to the growth of scar tissue in the liver that can occur in the context of a chronic hepatitis infection.

The term "pegylated IFNα2 mutants" as used herein means polyethylene glycol modified conjugates of IFNα2 mutants. The preferred polyethylene-glycol-IFNα2 mutant conjugates are reversible conjugate that are slowly converted to the drugs in physiological conditions, such as are prepared according to the methods described in WO2004089280. Other IFNα2 mutant conjugates can be prepared by coupling an IFNα2 mutant to a water-soluble polymer. A non-limiting list of such polymers includes other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon alpha-polymer conjugates are described in U.S. Pat. No. 4,766,106 and U.S. Pat. No. 4,917,888.

As defined herein, a "microarray" refers to a plurality of isolated nucleic acid molecules or oligonucleotide probes attached to a support where each of the nucleic acid molecules or oligonucleotide probes is attached to a support in unique pre-selected region. The term "nucleic acid" is interchangeable with the term "polynucleotide". The term "polynucleotide" refers to a chain of nucleotides. Preferably, the chain has from about 20 to 10,000 nucleotides, more preferably from about 150 to 3,500 nucleotides. The term "probe" refers to a polynucleotide sequence capable of hybridizing with a gene transcript or complement thereof to form a polynucleotide probe/gene transcript complex.

The term "gene" includes a region that can be transcribed into RNA, as the invention contemplates detection of RNA or equivalents thereof, for example, cDNA and cRNA. A gene of the invention includes, but is not limited to, genes specific for or involved in a particular biological process and/or indicative of a biological process, such as apoptosis, differentiation, stress response, aging, proliferation, etc.; cellular mechanism genes, e.g., cell-cycle, signal transduction, metabolism of toxic compounds, and the like; disease associated genes, e.g., genes involved in cancer, multiple-sclerosis, infection and the like. For example, the gene can be an oncogene, whose expression within a cell induces that cell to become converted from a normal cell into a tumor cell. Further examples of genes include, but are not limited to, cytokine genes, prion genes, genes encoding molecules that induce angiogenesis, genes encoding adhesion molecules, genes encoding cell surface receptors, genes encoding proteins that are involved in metastasizing and/or invasive processes, genes of proteases as well as of molecules that regulate apoptosis and the cell cycle.

According to the present invention, the level of a gene transcript can be determined by measuring the level of the gene transcript, e.g., RNA, using semi-quantitative methods such as microarray hybridization or more quantitative methods such as quantitative qPCR.

As used herein, the term "regulating expression and/or activity" generally refers to any process that function to control or modulate the quantity or activity (functionality) of a cellular component. Static regulation maintains expression and/or activity at some given level. Upregulation refers to a relative increase in expression and/or activity. Accordingly, downregulation refers to a relative decrease in expression and/or activity. Downregulation is synonymous with inhibition of a given cellular component's activity.

Characteristics of the Improved IFNα2 Polypeptides of the Invention

Three single mutations (H57A, E58A, Q61A) (SEQ ID NO: 5) were introduced into IFNα2 which specifically increase its binding affinity towards the IFNAR1 receptor by about 30-fold compared to the wild-type protein (SEQ ID: NO 2). The affinity of the mutant IFNα2 protein, as used herein designated HEQ, is similar to that measured for IFNβ (Table 3), which is much above that for any other interferon subtype. Evaluating the biological activity of HEQ clearly demonstrates that it gained very similar characteristics of IFNβ (SEQ ID NO: 3). Thus, HEQ promotes only a-2 fold increase in its antiviral potency, but a 25-fold increase in its antiproliferative potency relative to IFNα2-wt (SEQ ID NO: 2) (Table 4).

Two additional sets of mutations were introduced into the same positions in IFNα2 as HEQ: H57M, E58D, Q61L, herein designated MDL (SEQ ID NO: 10), and H57Y, E58N, Q61S, herein designated YNS (SEQ ID NO: 11). The antiviral activity of both is within 3-fold of wild-type (Table 4). However, their antiproliferative activity is higher than that of HEQ of IFNβ. For MDL, the activity is 40-fold higher compared to wt, and for YNS it is 160-fold higher in WISH cells and 70-fold higher in MDA231 cells, which is 3-7 fold that than measured for IFNβ (SEQ ID NO: 3).

The gene-transcription profile of HEQ (SEQ ID NO: 5) was monitored by oligonucletide microarray experiments. HEQ gene activation is much higher than that of IFNα2 at the same protein concentration, similar to gene activation recorded for IFNβ (SEQ ID NO: 3). YNS or HEQ could potentially be more effective drugs in the treatment of disease in comparison with either IFNα2-wt or IFNβ. The advantage of YNS and HEQ over IFNα2-wt is in its greater antiproliferative specificity, which could help in reducing side-effects and in the treatment of cancer or multiple-sclerosis. The advantage of YNS is its higher antiproliferative effect compared to IFNβ, particularly as measured in human breast cancer cells, MDA231.

The present invention further provides a quadruple mutant N65A, L80A, Y85A, Y89A (SEQ ID NO: 6), as used herein designated NLYY, which has a 1000-fold reduced antiproliferative activity and a 100-fold reduced antiviral activity compared to the wild-type protein but still binds to IFNAR2 at wild-type affinity (Table 2).

The present invention provides an IFNα2 protein comprises a substitution of the C terminal ESLRSKE to KRLK-SKE (SEQ ID NO: 7), as used herein designated α8-tail. The α8-tail mutant was engineered to have the tail of interferon α8 in order to optimize the electrostatic binding energy between IFNα2 and its receptor IFNAR2. Binding measurements have shown that the α8-tail mutant has a 18 fold higher binding affinity to IFNAR2 compared with wild-type Table 2). The antiviral activity of the α8-tail mutant is 3-fold higher and the antiproliferative activity is 10-fold higher compared to wild-type (Table 2).

The specific mutations of the three IFNα2 mutants of the invention are each located at a different position on the protein, and therefore can be combined to yield additional, or increased effects. The present invention provides variants comprise a combination of the triple mutant HEQ (SEQ ID NO: 5); MDL (SEQ ID NO: 10) or YNS (SEQ ID NO: 11), and the substitution of the C terminal of ESLRSKB to KRLK-SKE (SEQ ID NO: 7). These variants (SEQ ID NOS: 8, 12 and 13), may prove to be more efficient in treating cancer, specifically as their antiproliferative activity is increased. Moreover, their higher binding potency, may overcome the problem of receptor down-regulation in cancer cell. Since HEQ is composed of three single point mutations to Ala, and the α8-tail mutant comprises a replacement of the C-terminal of IFNα2 with the C-terminal of the native IFNα8, the possibility of specific immunogenic response is small.

The present invention further provides a variant comprises a combination of the quadruple mutant N65A, L80A, Y85A, Y89A and the substitution of the C terminal of ESLRSKE to KRLKSKE (SEQ ID NO: 9), with an increased binding affinity to IFNAR2, but with very low biological activity. This IFNα2 variant is an IFN antagonist, which blocks the natural activity of IFNs through there receptors.

The improved IFNα2 compositions of the present invention comprise IFNα2 mutant polypeptides, or fragments, analogs, derivatives, and variants thereof, that have at least 2-fold, preferably at least 10-fold, and more preferably at least 100-fold, even more preferably 1000-fold, greater specific activity than that of a reference IFNα2 wild-type composition. In certain embodiments, the IFNα2 compositions of the present invention have antagonistic activity to wild-type IFNα2.

The Antagonists of the Invention

An IFNα antagonist is defined to be any substance that is capable of interfering with a biological activity of IFNα in vivo. It is not necessary that the antagonist completely neutralizes the IFNα activity, but only that it do so to a degree sufficient to exert an IDDM or SLE therapeutic activity in vivo. IFNα is known to possess a plurality of biological activities. The antagonists for use herein will reduce, inhibit or neutralize any one or more of these activities. Ordinarily the antagonist will interfere with at least one (and preferably all) of the antiviral, antiproliferative or the immunomodulatory activity of IFNα.

The antagonists generally are selected from several categories: a soluble form of the alpha interferon receptor, anti-alpha interferon receptor antibodies which block alpha interferon from binding or properly interacting with its receptor, antibodies capable of binding and neutralizing alpha interferon itself, and non-interferon polypeptides which compete with alpha interferon for receptor binding sites but which do not themselves demonstrate substantial alpha interferon activity. The antagonists of the present invention are mutants of IFNα that antagonize IFNα and IFNβ activity.

IFNα2 Mutagenesis

The effects of altering amino acids at specific positions may be tested experimentally by introducing amino acid substitutions and testing the altered IFNα2 polypeptides for biological activity using assays described herein. Any technique for mutagenesis known in the art can be used, including but not limited to, chemical mutagenesis, in vitro site-directed mutagenesis, using, for example, the QuikChange Site-Directed Mutagenesis Kit (Stratagene), etc. Techniques such as alanine scanning mutagenesis are particularly suited for this approach.

Nucleic Acids

The present invention further provides nucleic acid molecules encoding the improved IFNα2 polypeptides of the invention.

A nucleic acid molecule can be produced using recombinant DNA technology (e.g., polymerase chain reaction (PCR) amplification, cloning) or chemical synthesis. Nucleic acid sequences include natural nucleic acid sequences and homologs thereof, comprising, but not limited to, natural allelic variants and modified nucleic acid sequences in which nucleotides have been inserted, deleted, substituted, and/or inverted in such a manner that such modifications do not substantially interfere with the nucleic acid molecule's ability to encode the recombinant IFNα2 polypeptides the present invention.

A polynucleotide or oligonucleotide sequence can be deduced from the genetic code of a protein, however, the degeneracy of the code must be taken into account, and nucleic acid sequences of the invention also include sequences, which are degenerate as a result of the genetic code, which sequences may be readily determined by those of ordinary skill in the art.

The terms "nucleic acid" and "polynucleotide" as used herein refer to an oligonucleotide, polynucleotide or nucleotide and fragments or portions thereof, and to DNA or RNA of genomic or synthetic origin, which may be single- or double-stranded, and represent the sense or antisense strand. The term should also be understood to include, as equivalents, analogs of either RNA or DNA made from nucleotide analogs, and, as applicable to the embodiment being described.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

As used herein, highly stringent conditions are those, which are tolerant of up to about 5% to about 25% sequence divergence, preferably up to about 5% to about 15%. Without limitation, examples of highly stringent (−10° C. below the calculated Tm of the hybrid) conditions use a wash solution of 0.1×SSC (standard saline citrate) and 0.5% SDS at the appropriate Ti (incubation temperature) below the calculated Tm of the hybrid. The ultimate stringency of the conditions is primarily due to the washing conditions, particularly if the hybridization conditions used are those, which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSC (or 6×SSPE), 5×Denhardt's reagent, 0.5% SDS, 100 µg/ml denatured, fragmented salmon sperm DNA at an appropriate Ti. (See generally Sambrook et al., Molecular Cloning: A Laboratory Manual, 2d edition, Cold Spring Harbor Press (1989) for suitable high stringency conditions).

Stringency conditions are a function of the temperature used in the hybridization experiment and washes, the molarity of the monovalent cations in the hybridization solution and in the wash solution(s) and the percentage of formamide in the hybridization solution. In general, sensitivity by hybridization with a probe is affected by the amount and specific activity of the probe, the amount of the target nucleic acid, the detectability of the label, the rate of hybridization, and the duration of the hybridization. The hybridization rate is maximized at a Ti of about 20° C.-25° C. below Tm for DNA:DNA hybrids and about 10° C.-15° C. below Tm for DNA:RNA hybrids. It is also maximized by an ionic strength of about 1.5M $Na^+$. The rate is directly proportional to duplex length and inversely proportional to the degree of mismatching.

Specificity in hybridization, however, is a function of the difference in stability between the desired hybrid and "background" hybrids. Hybrid stability is a function of duplex length, base composition, ionic strength, mismatching, and destabilizing agents (if any). The Tm of a perfect hybrid may be estimated for DNA:DNA hybrids using the equation of Meinkoth et al., (Anal Biochem. 1984; 138(2):267-84).

Expression and Purification of Improved IFNα2 Polypeptides

There are several ways to express and purify recombinant human IFNα2 in bacteria, in particular in *E. coli*, to obtain IFNα2 polypeptides having improved agonist or antagonist activity. Known methods can be used to express the cloned genes in bacteria. To obtain high-level expression of a cloned eukaryotic gene in a prokaryotic system, it is preferable to construct expression vectors that contain, a strong promoter to direct mRNA transcription.

Examples of regulatory regions suitable for this purpose are the promoter and operator region of the *E. coli* beta-glucosidase gene, the *E. coli* tryptophan biosynthetic pathway, or the leftward promoter from phage A. The inclusion of selection markers in DNA plasmids transformed in *E. coli* is also useful. Examples of such markers include the genes specifying resistance to ampicillin, tetracycline, or chloramphenicol. Post-translational modifications, such as glycosylation, do not occur in the prokaryotic cell expression system *E. coli*. In addition, proteins with complex disulfide patterns are can be misfolded when expressed in *E. coli*. With the prokaryotic system, the expressed protein is either present in the cell cytoplasm in an insoluble form, in so-called inclusion bodies, found in the soluble fraction after the cell has lysed, or is directed into the periplasm by the addition of appropriate secretion signal sequences. If the expressed protein is in insoluble inclusion bodies, solubilization and subsequent refolding of the inclusion bodies are usually required.

Many prokaryotic expression vectors are known to those of skill in the art and are commercially available, such as pKK223-3 (Pharmacia Fine Chemicals, Uppsala, Sweden), pKK233-2 (Clontech, Palo Alto, Calif., USA), and pGEM1 (Promega Biotech, Madison, Wis., USA). Promoters commonly used in recombinant microbial expression systems include the beta-lactamase (penicillinase) and lactose promoter system (Chang, A. C. et al. 1978, Nature 275: 617-624). The tryptophan (trp) promoter system, and the Tac promoter (Sambrook, J. F. et al., Molecular Cloning: A Laboratory Manual, Cold Spring Harbor Laboratory, Cold Spring Harbor, N.Y. 1989). Another useful bacterial expression system employs the lambda phage pL promoter and clts857 thermoinducible repressor (Bernard et al., 1979, Gene 5: 59-76).

Currently the following protocol was used: The gene coding for IFNα2 was cloned into a two-cistron expression vector based on the pT7T3-18U plasmid, to which we added a second cistron just upstream from the starting codon. The second cistron is of the first 9 amino acids of the lpp 5' gene including its SD site flanked by XbaI and NdeI restriction sites. The reason for inserting a second cistron was to improve the yield of heterologous protein expression. In addition, to improve the level of expression, the codons for the first 23 amino-acids were changed into: TGT GAT CTG CCG CAG ACT CAC TCT CTG GGT TCT CGT CGT ACT CTG ATG CTG CTG GCT CAG ATG CGT CGT (SEQ ID NO: 14). Proteins are expressed in BL21 cells, overnight in rich medium. IFNα2 is found in the inclusion bodies, which are dissolved in 8 M urea containing 5 mM DTT. IFNα2 was refolded by a 20-fold dilution over night. Protein purification is carried using standard methodologies. Typical yields of protein were 10 mg/L cell culture. IFNα2 runs as a single band of 18 kDa on SDS-PAGE.

Analogs, Fragments, Derivatives and Variants of Improved IFNα2 Polypeptides

An analog, fragment, derivative, or variant of the improved IFNα2 polypeptides of the present invention may be: (i) one in which one or more of the amino acid residues are substituted with a conserved or non-conserved amino acid residue; or (ii) one in which one or more of the amino acid residues includes a substitute group; or (iii) one in which the improved IFNα2 polypeptide is fused with another compound, such as a compound to increase the half-life of the improved IFNα2 polypeptide (for example, polyethylene glycol); or (iv) one in which additional amino acids are fused to the mature, improved IFNα2 polypeptide, such as a leader or secretory sequence or a sequence which is employed for purification of the mature, improved IFNα2 polypeptide; or (v) one in which the improved IFNα2 polypeptide sequence is fused with a larger polypeptide, i.e., human albumin, an antibody or Fc, for increased duration of effect. Such analogs, fragments, derivatives, and variants are deemed to be within the scope of those skilled in the art from the teachings herein. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamin, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Non-conservative substitutions would not be made for conserved amino acid residues or for amino acid residues residing within a conserved protein domain. Fragments or biologically active portions include polypeptide fragments suitable for use as a medicament, as a research reagent, and the like. Fragments include peptides comprising amino acid sequences sufficiently similar to or derived from the amino acid sequences of an improved IFNα2 polypeptide of this invention and exhibiting at least one activity of that polypeptide, but which include fewer amino acids than the full-length polypeptides disclosed herein. Typically, biologically active portions comprise a domain or motif with at least one activity of the polypeptide. Such biologically active portions can be prepared synthetically or by recombinant techniques and can be evaluated for one or more of the functional activities of a polypeptide of this invention by means disclosed herein and/or well known in the art.

Preferred derivatives of the present invention include improved IFNα2 polypeptides that have been fused with another compound, such as a compound to increase the half-life of the polypeptide and/or to reduce potential immunogenicity of the polypeptide (for example, polyethylene glycol, "PEG"). The PEG can be used to impart water solubility, size, slow rate of kidney clearance, and reduced immunogenicity to the fusion protein. See, e.g., U.S. Pat. No. 6,214,966. In the case of PEGylations, the fusion of the improved IFNα2 polypeptide to PEG can be accomplished by any means known to one skilled in the art. For example, PEGylation can be accomplished by first introducing a cysteine mutation into the improved IFNα2 polypeptide, followed by site-specific derivatization with PEG-maleimide. The cysteine residue can be added to the C-terminus of the improved IFNα2 polypeptide. See, e.g., Tsutsumi, Y. et al., (2000) Proc. Natl. Acad. Sci. USA 97: 8548-8553.

Variants of the improved IFNα2 polypeptides of this invention include polypeptides having an amino acid sequence sufficiently similar to the amino acid sequence of the original improved IFNα2 polypeptides or combinations thereof. Variants include improved IFNα2 polypeptides that differ in amino acid sequence due to mutagenesis. Variants with improved activity can be identified by screening combinatorial libraries of mutants, for example truncation or point mutants, of improved IFNα2 polypeptides of this invention.

In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential variant amino acid sequences is expressible as individual polypeptides, or, alternately, as a set of larger improved IFNα2 polypeptides (for example, for phage display) containing the set of sequences therein. There are a variety of methods that can be used to produce libraries of potential variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential variant sequences. Methods for synthesizing degenerate oligonucleotides are known in the art (see, e.g. Itakura, K. et al. 1984, Annu. Rev. Biochem. 53: 323-356).

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of improved IFNα2 polypeptides for specific activity. The most widely used techniques, which are amenable to high throughput analysis for screening large gene libraries typically include cloning the gene library into replicable expression vectors, transforming appropriate cells with the resulting library of vectors and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify the desired variants.

Pharmaceutical Compositions of the Invention

The invention also provides pharmaceutical compositions that can be administered to a patient to achieve a therapeutic effect. Pharmaceutical compositions of this invention can be prepared for administration by combining an improved IFNα2 polypeptide, having the desired degree of purity in a pharmaceutically effective amount, with pharmaceutically acceptable carriers.

The improved IFNα2 polypeptides and pharmaceutical compositions of the present invention are useful for parenteral (e.g., intravenous, intramuscular and subcutaneous), topical, oral, inhalable, or local administration.

The improved polypeptides of the invention can be used in pharmaceutical compositions, for any suitable method of administration, including but not limited to intravenous, subcutaneous, intramuscular, or intrathecal administration. Thus, the above described polypeptides preferably will be combined with an acceptable sterile pharmaceutical carrier, such as five percent dextrose, lactated Ringer's solution, normal saline, sterile water, or any other commercially prepared physiological buffer solution designed for intravenous infusion. It will be understood that the selection of the carrier solution, and the dosage and administration of the composition, will vary with the subject and the particular clinical setting, and will be governed by standard medical procedures.

In accordance with the methods of the present invention, these pharmaceutical compositions may be administered in amounts effective to inhibit or ameliorate the pathological consequences or symptoms associated with MS, cancer, IDDM or SLE.

Administration of the improved IFNα2 polypeptides of the present invention may be by bolus intravenous injection, by constant intravenous infusion, or by a combination of both routes. Alternatively, or in addition, the improved IFNα2 polypeptides mixed with appropriate excipients may be taken into the circulation via an intramuscular site.

Clearly, polypeptides are less suitable for oral administration due to susceptibility to digestion by gastric acids or intestinal enzymes, however in certain embodiments specific formulations may be used for oral administration.

In preparing the compositions in oral liquid dosage forms (e.g., suspensions, elixirs and solutions), typical pharmaceutical media, such as water, glycols, oils, alcohols, flavoring agents, preservatives, coloring agents and the like can be employed. Similarly, when preparing oral solid dosage forms (e.g., powders, tablets and capsules), carriers such as starches, sugars, diluents, granulating agents, lubricants, binders, disintegrating agents and the like will be employed. Due to their ease of administration, tablets and capsules represent a desirable oral dosage form for the pharmaceutical compositions of the present invention.

Polypeptides are less suitable for topical administration, however for local treatment specific formulations may be used.

For topical administration, the improved IFNα2 polypeptides of the present invention may be formulated using bland, moisturizing bases, such as ointments or creams. Examples of suitable ointment bases are petrolatum, petrolatum plus volatile silicones, lanolin and water in oil emulsions.

For administration by inhalation, the IFNα2 polypeptides for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base such as lactose or starch.

The improved IFNα2 polypeptides and pharmaceutical compositions of the present invention are particularly useful for intravenous administration. The compositions for administration will commonly comprise a solution of the improved IFNα2 polypeptide dissolved in a pharmaceutical acceptable carrier, preferably in an aqueous carrier. A variety of aqueous carriers can be used, e.g., buffered saline and the like. These solutions are sterile and generally free of undesirable matter. The compositions may be sterilized by conventional, well-known sterilization techniques. A typical pharmaceutical composition for intravenous administration can be readily determined by one of ordinary skill in the art. The amounts administered are clearly protein specific and depend on its potency and pharmacokinetic profile. Actual methods for preparing parenterally administrable compositions will be known or apparent to those skilled in the art and are described in more detail in such publications as Remington's Pharmaceutical Science, 18t ed., Mack Publishing Company, Easton, Pa., 1990.

The compositions containing the improved IFNα2 polypeptides of the invention or a cocktail thereof (i.e., with other proteins) can be administered in therapeutic treatments. In therapeutic applications, compositions are administered to a patient suffering from MS, cancer, and disorders associated with increased IFNα2 expression of IFNα2 in an amount sufficient to cure or at least partially arrest the disorder. An amount adequate to accomplish this is defined as a "therapeutically effective dose". Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the improved IFNα2 polypeptides of this invention to effectively treat the patient. Generally, depending on the intended mode of administration, the pharmaceutical acceptable compositions will contain about 1% to about 99% by weight of an improved IFNα2 polypeptide of the invention, and 99% to 1% by weight of a suitable pharmaceutical excipient or carrier. Preferably, the composition will be about 5% to 75% by weight of an improved IFNα2 polypeptide (s) of the invention, with the rest being suitable pharmaceutical excipients or carriers.

The improved IFNα2 polypeptides of the present invention, or their pharmaceutical acceptable compositions, are administered in a therapeutically effective amount, which will vary depending upon a variety of factors including the specific activity of the particular improved IFNα2 polypeptide employed; the metabolic stability and length of action of the improved IFNα2 polypeptide; the age, body weight, general health, sex, and diet of the patient; the mode and time of administration; the rate of excretion; the drug combination; the severity of the particular disease-states; and the host undergoing therapy. Generally, a therapeutically effective daily dose is from about 0.1 μg to about 1000 μg/kg of body weight per administration of an improved IFNα2 polypeptide of the invention, preferably, from about 0.5 μg to about 100 μg/kg of body weight per administration. For example, for administration to a 70 kg person, the dosage range would be from about 10 μg to about 100 μg per administration of an improved IFNα2 polypeptide of the invention depending on the treatment regimen. For example, if the improved IFNα2 polypeptide of the invention or formulation containing the polypeptide is administered from one to several times a day, then a lower dose would be needed than if a formulation was administered weekly, or monthly or less frequently.

It is anticipated that IFNα2 polypeptides of the present invention are administered in proper doses. Doses are generally adjusted to at or below the maximum tolerated dose (MTD). Signs indicative of interferon toxicity are noted to be as to hematologic toxicity, anemia, thrombocytopenia, leukopenia: as to gastrointestinal toxicity, diarrhea, dyspepsia, dysphagia, N/V, abdominal pain; as to liver toxicity increases in bilirubin, alk phos and LFTs; as to kidney and bladder, microscopic hematuria, pyuria, azotemia, proteinuria, acute renal failure, nephrotic syndrome, glycosuria, albuminuria; as to pulmonary, orthopnea, dyspnea, bronchospasm, coughing, pulmonary edema, ARDS; as to cardiac toxicity syncope, MI, SVT, bradycardia, tachycardia, dizziness, hyptoension, hypertension. Neurological toxicity are confusion, tremors, numbness, paresthesia, inability to concentrate, somnolence, hallucinations, encephalopathy, seizure, coma, psychomotor retardation, memory dysfunction, dry mouth, sweating, personality disorder, agitation, neuropathy, depression, anxiety, aphasia, retinal infarction with vision loss, eye pain, hemianopsis, taste change, headache, syncope, insomnia. Dermal toxicity of skin rash, uiticaria, epidermal necrosis, maculopapular rash is noted. Metabolic toxicity manifests as hyperglycemia. In addition coagulation is monitored for increase in PT/PTT. Also the presence of phyarngitis, alopecia, fatigue, malaise, anorexia, weight loss, fever, chills, myalgia, arthralgia, cyanosis are potential toxic responses to interferon.

Therapeutic Indications

Multiple Sclerosis (MS)

The two forms of IFN, IFNβ1a and IFNβ1b, are approved for the treatment of relapsing remitting MS. IFN-β is also used to treat genital warts. The improved IFNα2 polypeptides of this invention are useful in the above diseases, disorders, or conditions, and are also useful for the treatment of other forms of MS, including secondary progressive MS, primary progressive MS, and progressive relapsing MS. By useful it is meant that the improved IFNα2 polypeptides are useful for treatment of disease, e.g., either to prevent disease, or to prevent disease progression to a more severe state, or to ameliorate or reduce a symptom or consequence of disease, such as MS.

Cancer

Despite the numerous advances in cancer treatment, the well-known life style changes that can greatly reduce the risk of cancer, and the early warning signs that some cancers provide, many patients still develop cancer for which no conventional therapies are available that offer any reasonable hope of cure or significant palliation. IFNα2 is known to have anti-cancer effects.

A person suffering from advanced cancer may exhibit one or more of the following signs or symptoms: presence of cancerous tumor, fatigue, pain, decreased performance status from tumor burden, and the well-known symptoms associated with each specific cancer.

To practice the invention, IFNα2 mutants are administered to the patient exhibiting one of more of the above signs or symptoms in amounts sufficient to eliminate or at least alleviate one or more of the signs or symptoms.

Hepatitis Virus (HCV) Infection

Current therapies to treat HCV infection suffer from certain drawbacks. Dosing regimens involving daily (QD), every other day (QOD), or thrice weekly (TIW) injections of IFN-α over extended treatment periods suffer from one or more of the following drawbacks: (1) the dosing regimens are uncomfortable to the patient and, in some cases, result in reduced patient compliance; (2) the dosing regimens are often associated with adverse effects, causing additional discomfort to the patient and, in some cases, resulting in reduced patient compliance; (3) the dosing regimens result in "peaks" (Cmax) and "troughs" (Cmin) in serum IFN-α concentration, and, during the "trough" periods, virus can replicate, and/or infect additional cells, and/or mutate; (4) in many cases, the log reduction in viral titer during the early viral response is insufficient to effect a sustained viral response that ultimately results in clearance of the virus. The present invention could have significant impact in the improvement of the therapeutic potential of treating a hepatitis virus infection.

Insulin Dependent Diabetes Mellitus (IDDM)

The etiology of IDDM is a matter of great debate. It appears to be multifactorial, including genetic predisposition and environmental influences. Strong associations have been identified between IDDM and specific HLAs coded by the major histocompatibility complex region located on the short arm of chromosome 6. The major high-risk alleles are DR3 and DR4. The environmental influences thought to be important include viruses, and several lines of evidence support this view. Certain diabetogenic or associated viruses (mumps, measles, rubella, encephalomyocarditis M, coxsackievilus B, and rheovirus) have been associated epidemiologically with the development of IDDM or can cause diabetes when inoculated into rodents. Diabetogenic viruses can directly infect B cells in culture. In addition, coxsackievirus B4 has been isolated from the pancreas of a boy with new-onset IDDM who died of severe ketoacidosis, and this virus produced diabetes in experimental animals together with viral antigens in the B cells of the infected animals. B cells of IDDM patients' secreted alpha interferon, thus antagonist IFNα2 polypeptides of this invention could have significant impact in the improvement of the therapeutic potential of IDDM.

Lupus Erythematosus (LE)

LE is an autoimmune disease that causes inflammation and damage to various body tissues and parts, including joints, kidneys, heart, lungs, brain, blood vessels, and skin. The most common symptoms of LE include achy or swollen joints (arthritis), fever, prolonged or extreme fatigue, skin rashes and kidney problems. Even though the cause of LE is still unknown, LE is believed to be caused by a combination of genetic, environmental and possibly hormonal factors. LE can be characterized by periods of illness or flares, and periods of wellness or remission. Accordingly, the goals of effective treatment of LE are to prevent flares, minimize organ damage and complications, and maintain normal bodily functions. Commonly prescribed medications for LE include nonsteroidal anti-inflammatory drugs (NSAIDs), acetaminophen, corticosteroids, antimalarials and immunomodulating drugs. Because of the limited success of currently available medications and their potentially serious side effects, it is important to provide an alternative effective treatment for LE.

The composition of the invention may be effective in minimizing and/or eliminating various symptoms in LE patients.

Having now generally described the invention, the same will be more readily understood through reference to the following examples, which are provided by way of illustration and are not intended to be limiting of the present invention.

EXAMPLES

Methods (i) Site-directed mutagenesis. Site-directed mutagenesis was carried out by PCR amplification of the expression plasmid pT72Cα2 with 18-21 nucleotide primers containing the mutated codon using high fidelity polymerases pwo (Boehringer Mannheim) and pfu (Stratagene) as described previously (Piehler, J. & Schreiber, G. 1999, *J. Mol. Biol.* 294, 223-237). After phosphorylation and ligation, the mutated plasmids were transformed into *E. coli* TG1 cells. The sequence of the whole expressed gene containing the mutation was verified by DNA sequencing.

(ii) Protein expression and purification. IFNα2 and IFNAR2-EC were expressed in *E. coli* and purified by ion exchange and size-exclusion chromatography as described previously (Piehler, J. & Schreiber, G. 1999, *J. Mol. Biol.* 289, 57-67).

Protein concentrations were determined from the absorbance at 280 nm with $\epsilon_{280}=18070$ cm$^{-1}$M$^{-1}$ for IFNα2 and $\epsilon_{280}=26500$ cm$^{-1}$M$^{-1}$ for IFNAR2-EC. IFNAR1-EC was expressed in Sf9 insect cells and purified as described (Arduini, R. M. et al., 1999, *Protein Science* 8, 1867-1877).

Protein purity was analyzed by SDS-PAGE under non-reducing conditions. The concentration of active IFNα2 protein was determined for all mutants by analytical gel filtration with IFNAR2-EC as described previously (Piehler, J. & Schreiber, G. 1999, J. Mol. Biol. 289, 57-67). For ligand binding studies, IFNα2 and IFNβ were site-specifically labelled using maleimide chemistry. IFNβ was labelled directly at its free cysteine residue C17 by incubation of a 2-fold molar excess of Oregon Green 488 (OG488) maleimide (Molecular Probes) for 2 h in HBS. IFNα2 was labelled with OG488 after incorporating an additional cysteine residue (mutation S136C), which has been shown not to affect the interaction with IFNAR1-EC or IFNAR2-EC (Gavutis et al., 2005, Biophysical Journal 88(6): 4289-4302).

(iii) Growth and refolding of IFNα2-YNS mutant. *E. coli* were grown in 750 ml flask. The bacteria were centrifuged, resuspended in 30 ml lysis buffer and sonicated in bacteriology for 30" for five times. Following centrifugation at 16,000 rpm for 30', the pellet (inclusion bodies) was resuspend in 30 ml triton wash solution (0.5% triton, 50 mM Tris8 and 100 mM NaCl). The inclusion bodies were centrifuged at 25,000 g (14,500 rpm in ss34 sorval) and were washed for 4-5 times. A final wash was performed to get rid of triton, using 50 mM Tris (8.4) with 100 mM NaCl. The purified inclusion bodies were dissolved in 5 ml of 6M Guanidine for about 12 hr at 4° C. with gentle stirring. Following centrifugation at 25000 g for 20', the supernatant was kept and the pellet was discarded.

For refolding, the supernatant was diluted 1:20 in 0.8M Arginin pH 9.3, stirred slowly while gently on a vortex, and shaked at 20° C. for 2 hrs. Following centrifugation at 16,000 rpm for 20' and dialyzis against Tris 7.4, the protein was purified by ion-exchange chromatography to yield: 5 mg/L of pure protein.

(iv) Measurements of binding affinity. The interaction between recombinant IFNAR1-EC and IFNα2 was monitored by Reflectometric Interference Spectroscopy (RIfS) under flow-through conditions (Schmitt, H. M., et al., 1997, *Biosens. & Bioelectron.* 12, 809-816). This method detects biomolecular interaction at interfaces as a change in the apparent optical thickness of a thin silica layer. Binding to the surface is monitored as a shift in the interference spectrum. A shift of 1 pm corresponds to approximately 1 pg/mm protein on the surface. A second method applied for real time binding measurements was by SPR (surface plasmon resonance) using the ProteON (Biorad). All measurements were carried out using HBS (20 mM HEPES pH 7.5, 150 mM NaCl and 0.01% Triton X100) as a running buffer. Binding of the IFNAR1 receptor subunit to the chip surface was done by two methods. In one, the non-neutralizing anti-IFNAR1-EC mAb DB2 was coupled to the (amino-functionalized dextran AMD 500) surface via its exposed amino groups by amine-coupling chemistry. The IFNAR1-EC was affinity captured to the surface followed by cross-linking with a second mAb AA3. In a second method, the His-tagged tail of IFNAR1 was directly linked to the NTA surface of the chip. A detailed description of the method used for measuring the interferon—IFNAR2-EC interaction is given in (Piehler, J. and Schreiber, G. 2001, *Anal. Biochem.* 289, 173-186). For weak binding, the determination of the dissociation constant $K_D$ was obtained from the equilibrium response plotted against the protein concentration and fitted according to the law of mass action. For tighter binding interactions, the kinetic rate constants were determined and the affinity was calculated from the ratio $k_{off}/k_{on}=K_D$ as well as directly from the equilibrium response.

(v) Antiviralprotection activity assay. Antiviral activity of wild-type and mutant IFNα2 was assayed as the inhibition of the cytopathic effect of vesicular stomatitis virus (VSV) on human WISH cells (Evinger, M. et al., 1981, *Arch. Biochem. Biophys.* 210, 319-329). The relative activity of IFNα2-mutants was determined as the concentration needed for 50% protection of the cells relative to the concentration of wild-type IFNα2 needed for 50% protection.

(vi) Antiproliferative assay. The antiproliferative activity of IFNα2 on Daudi Burkitt's lymphoma cells was assayed as described (Piehler, J. et al., 2000, *J. Biol. Chem.* 275, 40425-40433). The cells were treated for 60 h with IFN. The number of living cells was then determined using a cell staining kit (Biological Industries Co, Israel) based on the colorimetric detection of the cleavage of the tetrazolium salt XTT into formazan. The antiproliferative assay on WISH cells was conducted by adding interferon at different dilutions to the growth media, and monitoring the cells density after 72 hr by crystal violet staining.

(vii) Errors. The error ($\sigma$) on $K_D$ for IFNα2-IFNAR2 binding as measured on RIfS is 20%, and for relative affinity (wt/mut) 30%. For IFNα2-IFNAR1, the error ($\sigma$) on $K_D$ is 35% and for relative affinity (wt/mut) 50%. Using 2$\sigma$ (95% confidence) as the basic confidence level, this would suggest that a minimum of a two-fold change could be seen as significant. The magnitude of the error ($\sigma$) for individual biological activity measurements (whether antiviral or antiproliferative) is 35%. Therefore, a 2$\sigma$ confidence level between two measurements would suggest that differences smaller than two-fold are within the experimental error.

(viii) Spotted oligonucleotide microarray experiments. Poly-L-lysine-coated glass microarrays containing almost 19,000 different probes (Compugen's human oligonucleotide set) were purchased from CAG (Center for Applied Genomics, New Jersey). The microarrays were probed with a mixture consisting of cyanine (Cy) 3 or Cy5-labeled cDNA representing IFN treatment versus no-treatment (control). WISH cells were treated with different IFNs for 16 hours and their RNA extracted (RNeasy Midi kit, Qiagen), 100 µg of which was subjected to reverse transcription (M-MLV H-point mutant RT enzyme, Promega) with aminoallyl-modified dUTP nucleotide (Ambion) mixed in the nucleotide mixture at a 4:1 aa-dUTP to dTTP ratio. The cDNA produced was labeled with the NHS-activated Cy3 or Cy5 fluorescent probe (Amersham), which binds to the aa-dUTP. Incorporation was assessed (Nanoprop spectrophotometer) and labeled cDNAs were mixed (treatment with one color and control with the other) at equivalent amounts of fluorescent dye (100 pmoles each), in final 2×SSC, 0.08% SDS and 6 µl of Blocking solution (Amersham), in 100 µl target volume, denatured at 95° C. for 3 minutes, chilled and applied between a raised cover slip (LifterSlip, Erie Scientific Company) and the array. Hybridization was done at 55° C. for 12 hours in the dark. Afterwards, the slide was washed five minutes in 2×SSC, 0.5% SDS at 55° C.; five minutes in 0.5×SSC at room temperature and a lastly five minutes in 0.05×SSC at room temperature. Then it was dried by spinning 3 minutes at 1000 rpm, and stored in the dark until scanned.

(ix) Microarray image and data analysis. Scanning of the hybridized microarrays was performed with DNA microarray scanner (Agilent). Automatic spot detection, background subtraction and intensity quantification was done with the SpotReader (Niles Scientific) software. Data normalization, filtering and cluster analysis was done with the GeneSpring (SiliconGenetics) software. The analysis is based on the treatment to control ratio of each spot, and includes such manipulations as data filtration by SpotReader output flags, an indication of the quality of the signal, relatively to the background (noise). Each treatment (condition) is represented by two dye swap microarray replicates. A starting list of interferon-modulated genes was integrated by genes beyond a 1.7 threshold in at least two conditions, tolerating only one 'absent' ('A') flag, which is indicative of a 'noisy' spot, in all conditions per gene. This criterion was chosen after realizing that genuine up- or down-regulation is observed in more than just one IFN treatment, so choosing two conditions as a minimum, a low stringency threshold is necessary to include ISGs modified at relatively low levels.

The list of these genes was exported into an Excel worksheet, and contained the mean treatment to control ratio value, the replicate values, t-test p-values, which is an estimate of the microarray technical error based on the distance between replicates, and the flag codes. Genes were then eye-screened for significance, by comparing the distance between each pair of replicates and between conditions, looking also at p-values and the occurrence of 'A' flag. This tedious analysis was necessary because statistical selection left clearly up-/down-regulated out, because of the relatively large noise produced for the low number of replicates per condition. A mean value beyond the 1.7-threshold having one of its replicates below this threshold, or with a large inter-replicate distance relative to the mean, and with no other conditions with similar and significant levels, was considered not a bona-fide modulation, but technical noise, and the gene was consequently excluded from the list. The final list consisted of 395 genes, upregulated or downregulated by interferons at 16 hours of treatment. Cluster analysis was done on this list after importing it back to GeneSpring.

Example 1

Characterization of the IFNα2-IFNAR1-EC Interaction Using an Optical Biosensor System The interaction of IFNAR1-EC to IFNα2 was investigated by label-free solid phase detection using RIfS. This technology requires the immobilization on the chip surface of one of the interacting compounds. The method successfully employed previously for IFNAR2-EC was used, where the receptor is immobilized using mAbs which are themselves immobilized to the surface via amino-coupling (Piehler, J. and Schreiber, G. 2001, *Anal. Biochem.* 289, 173-186). The non-neutralizing anti-IFNAR1-EC mAb DB2 was coupled to the amino-functionalized dextran AMD 500 surface via its exposed amino groups. The IFNAR1-EC was affinity-captured to the mAb surface followed by cross-linking with a second mAb AA3. The process as followed in real time RIFS is shown in FIG. 1A. The binding activity of IFNAR1-EC bound to the RIfS surface was determined by injecting IFNα2 protein at concentrations ranging from 0.12 to 4 µM. Due to the low binding affinity of IFNα2 to IFNAR1-EC kinetic data of association and dissociation could not be determined. Therefore, the binding affinity was determined from plotting the steady-state response versus the protein-concentration according to the law of mass action. This results in an affinity constant of 1.5 µM for wild type IFNα2 (Lamken, P. et al., 2004, *J Mol Biol* 341, 303-318).

Example 2

Mapping the Binding Site of IFNα2 for IFNAR1

Figures 3A, 3B:
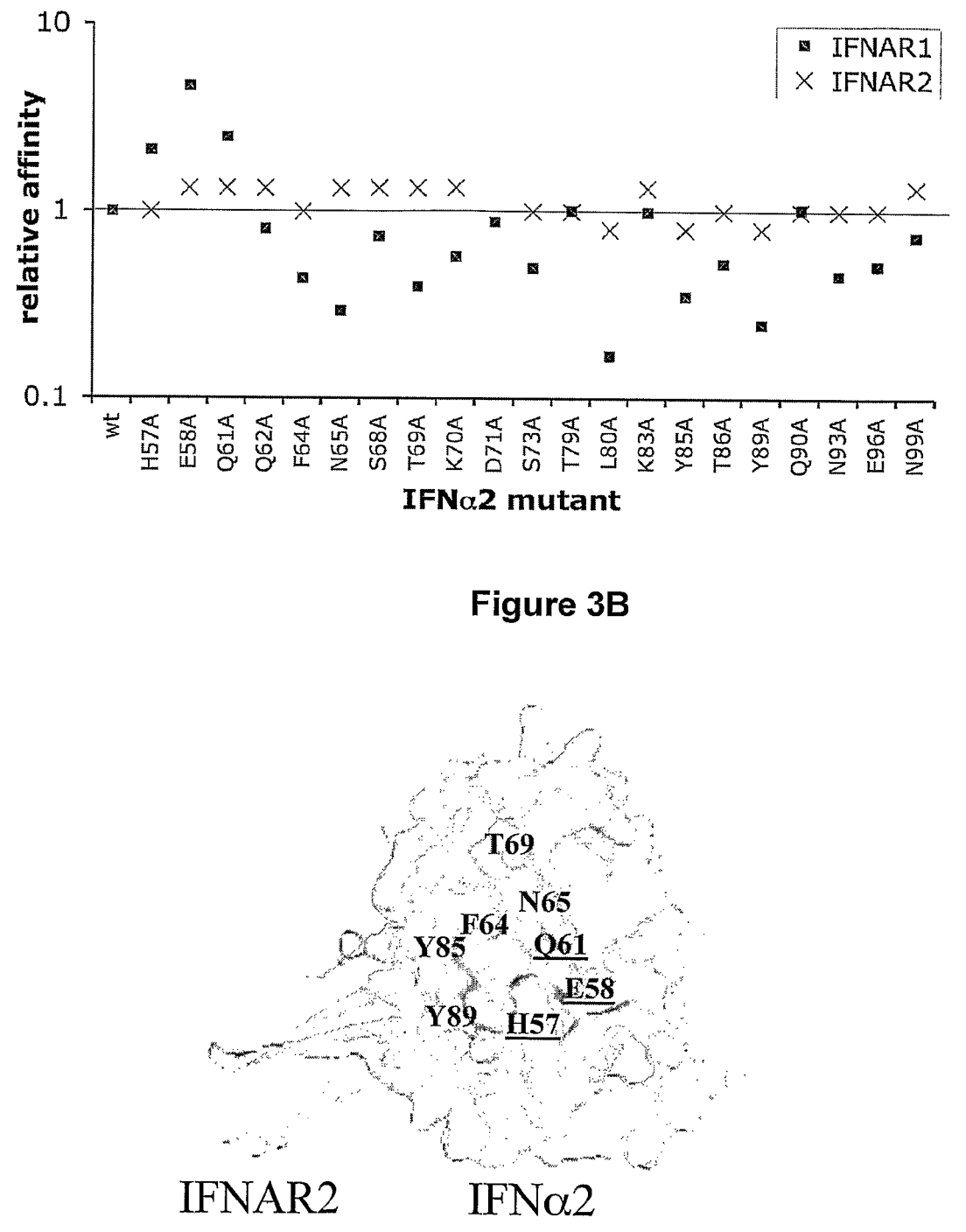

To locate the binding site of IFNAR1 on IFNα2, an Ala scan of most residues located on the B and C helices was performed (FIGS. 2 and 3). All together, 21 single point mutations were produced, and their binding affinity towards IFNAR2 and IFNAR1 were measured by RIFS or ProteON. As the mutations are located on the opposite surface of the IFNAR2 binding site on IFNα2, the binding affinities of the different mutant proteins towards IFNAR2 were very similar to that of wild-type IFNα2 (Table 1). This is assuring, as it validates the proper folding of all the mutant proteins, and their active concentrations. While binding of IFNα2 with IFNαR2-EC provides a clear kinetic signal, binding towards IFNAR1-EC is much weaker and has to be analyzed according to the refractive unit (RU) signal of the steady state affinity, by varying the concentration of the ligand. In this case, the knowledge of the correct and precise concentrations of all the IFNα2 proteins is essential. Therefore, all mutant protein concentrations were validated on an analytical gel-filtration column by their capacity to bind IFNAR2-EC. The results of all the binding measurements are summarized in Table 1 and 3 and FIG. 3A. Three single mutations cause an increase in binding (H57A, E58A, Q61A) while 6 mutations cause a decrease in binding (F64A, N65A, T69A, L80A, Y85A, Y89A). However, no hotspots for binding were identified, thus, none of the mutations lead to a change of over 5-fold in affinity. To corroborate the single-mutation effects, a triple-mutant containing the single-mutations L80A, Y85A, Y89A (herein designated as LYY) and a quadruple mutant N65A, L80A, Y85A, Y89A (SEQ ID NO: 6) (herein designated as NLYY) were prepared. Binding for these two mutant-proteins was below the threshold of the measurement.

TABLE 1

Thermodynamic and kinetic constants for the interactions of mutant
IFNα2 (B and C helix and the C-D loop) with IFNAR2-EC and IFNAR1-EC

| IFN mutant | $k_d$ [s$^{-1}$] | IFNAR2-EC $K_D$ [nM] | $K_D$ wt/mut | $^a\Delta G^0$ (kcal/mol) | $^b\Delta\Delta G^0$ (kcal/mol) | IFNAR1-EC $^cK_D$ [μM] | $K_D$ wt/mut | $^b\Delta G^0$ (kcal/mol) | $^c\Delta\Delta G^0$ (kcal/mol) |
|---|---|---|---|---|---|---|---|---|---|
| wt | 0.011 | 3 | | −11.6 | 0.0 | 1.6 | | −7.9 | |
| H57A | 0.015 | 4 | 1.0 | −11.4 | −0.2 | 0.69 | 2.1 | −8.4 | 0.5 |
| E58A | 0.011 | 3 | 1.3 | −11.6 | 0.0 | 0.31 | 4.7 | −8.8 | 0.9 |
| Q61A | 0.012 | 3 | 1.3 | −11.6 | 0.0 | 0.59 | 2.5 | −8.5 | 0.6 |
| Q62A | 0.009 | 3 | 1.3 | −11.6 | 0.0 | 1.82 | 0.8 | −7.8 | −0.1 |
| F64A | 0.013 | 4 | 1.0 | −11.4 | −0.2 | 3.33 | 0.4 | −7.4 | −0.5 |
| N65A | 0.012 | 3 | 1.3 | −11.6 | 0.0 | 5.00 | 0.3 | −7.2 | −0.7 |
| S68A | 0.010 | 3 | 1.3 | −11.6 | 0.0 | 2.00 | 0.7 | −7.8 | −0.2 |
| T69A | 0.012 | 3 | 1.3 | −11.6 | 0.0 | 3.70 | 0.4 | −7.4 | −0.6 |
| K70A | 0.010 | 3 | 1.3 | −11.6 | 0.0 | 2.56 | 0.6 | −7.6 | −0.3 |
| D71A | | | | | | 1.67 | 0.9 | −7.8 | −0.1 |
| S73A | 0.014 | 4 | 1.0 | −11.4 | −0.2 | 2.94 | 0.5 | −7.5 | −0.4 |
| T79A | 0.013 | 4 | 1.0 | −11.4 | −0.2 | 1.45 | 1.0 | −7.9 | 0.0 |
| L80A | 0.019 | 5 | 0.8 | −11.3 | −0.3 | 8.70 | 0.2 | −6.9 | −1.1 |
| K83A | 0.011 | 3 | 1.3 | −11.6 | 0.0 | 1.47 | 1.0 | −7.9 | 0.0 |
| Y85A | 0.019 | 5 | 0.8 | −11.3 | −0.3 | 4.17 | 0.4 | −7.3 | −0.6 |
| T86A | 0.016 | 4 | 1.0 | −11.4 | −0.2 | 2.78 | 0.5 | −7.6 | −0.4 |
| Y89A | 0.017 | 5 | 0.8 | −11.3 | −0.3 | 5.88 | 0.3 | −7.1 | −0.8 |
| Q90A | 0.013 | 4 | 1.0 | −11.4 | −0.2 | 1.43 | 1.0 | −7.9 | 0.0 |
| N93A | 0.016 | 4 | 1.0 | −11.4 | −0.2 | 3.23 | 0.5 | −7.5 | −0.5 |
| E96A | 0.013 | 4 | 1.0 | −11.4 | −0.2 | 2.86 | 0.5 | −7.5 | −0.4 |
| V99A | 0.010 | 3 | 1.3 | −11.6 | 0.0 | 2.00 | 0.7 | −7.8 | −0.2 |
| HEQ | 0.01 | 3 | 1.0 | −11.6 | 0.0 | 0.083 | 20 | −9.6 | 1.7 |
| NLYY | | | | | | | | | |
| α8-tail | 0.002 | 0.15 | 18 | −13.3 | 1.8 | | | | |
| $^d$IFNβ | 0.0012 | 0.1 | | −13.6 | | 0.066 | | −9.75 | 1.85 |

$^a\Delta G^0$ calculated from $\Delta G^0 = RT\ln K_D$;
$^b\Delta\Delta G^0 = \Delta G^0_{mut} - \Delta G^0_{wt}$;
$^cK_D$ is determined from equilibrium binding at the surface;
$^d$Data are from Lamken et al., 2004, J. Mol. Biol. 341, 303-318.

Example 3

Antiproliferative and Antiviral Activity of IFNα2 Mutants

Figure 4:
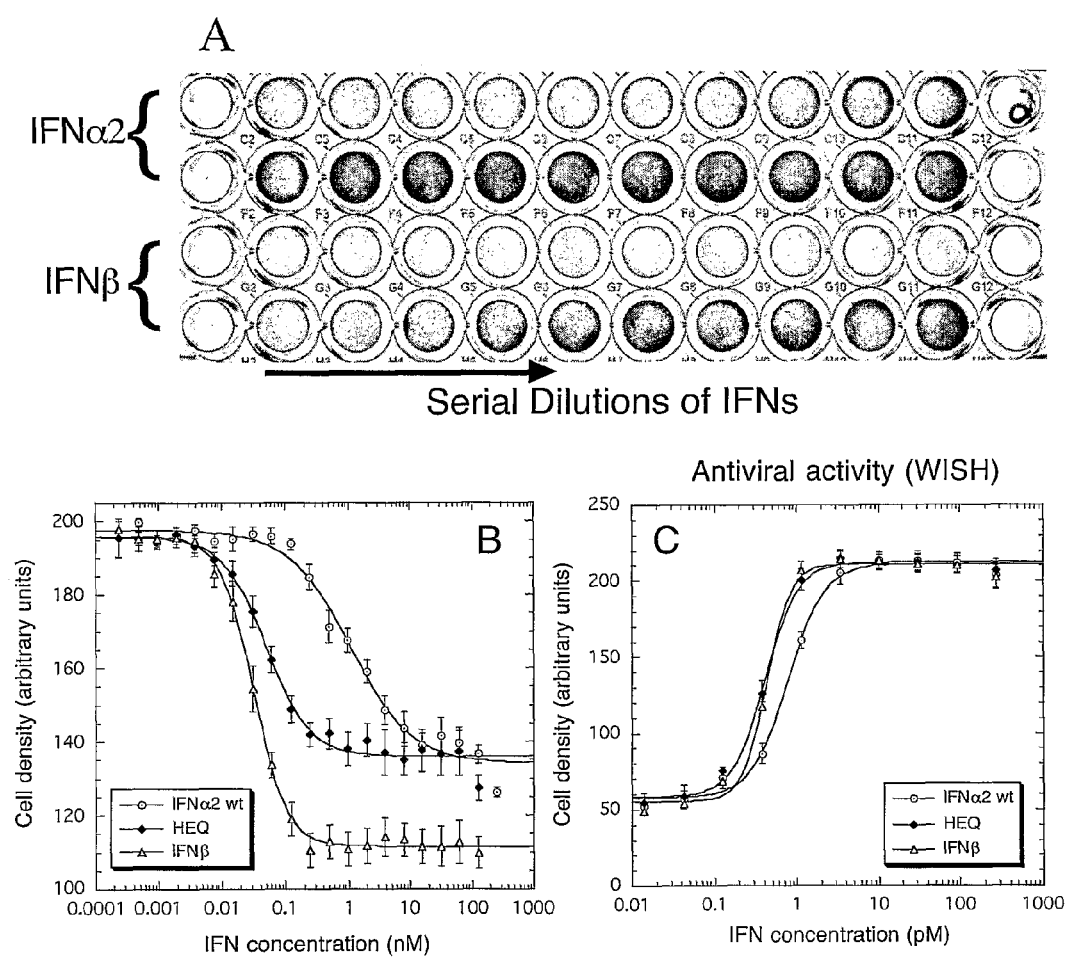
FIGS. 4A-4C show concentration dependence of the antiviral and antiproliferative response of interferons on WISH cells.

The antiviral activity was assayed as the inhibition of the cytopathic effect of vesicular stomatitis virus (VSV) on WISH cells (human epithelial cell line of amniotic origin). The antiproliferative activity was determined both on WISH cells and on Daudi cells, as the 50% inhibition of cell growth (as described in Methods). FIG. 4A shows the outcome of applying a serial dilution of concentrations of IFNα2 and IFNβ for 72 hr on the intensity exhibited by WISH cells after staining, from which the concentration of interferon promoting an antiproliferative effect can be deduced. The wells were scanned for densitometry analysis, and the results were plotted versus the protein-concentration applied (FIG. 4B). The same was done to determine the antiviral potency of interferons on WISH cells (FIG. 4C). The 50% activity point as well as the rate of change in activity (slope) were deduced from an IFN dose response curve, Eq. 1.

$$y = A_0 + A/(1+(c/c_{50})^s) \quad [\text{Eq. 1}]$$

wherein y is the transmittance which relates to the number of cells, $A_0$ is the offset, A is the amplitude, c is the concentration, $c_{50}$ is the concentration giving 50% activity, and s is the slope. The average IFNα2 and IFNβ concentrations promoting 50% antiviral protection are 0.85 and 0.43 pM respectively (averaged over 6 experiments). The average IFNα2 and IFNβ concentrations promoting 50% antiproliferative activity are 1360 and 29 pM (averaged over 17 and 7 experiments respectively). Interestingly, the IFNα2 concentration promoting 50% antiproliferative activity in Daudi cells is only 0.5 pM (Table 2), which is over a 1000-fold lower than that measured for WISH cells highlighting the importance of using the same cell line for all experiments.

Figure 5:
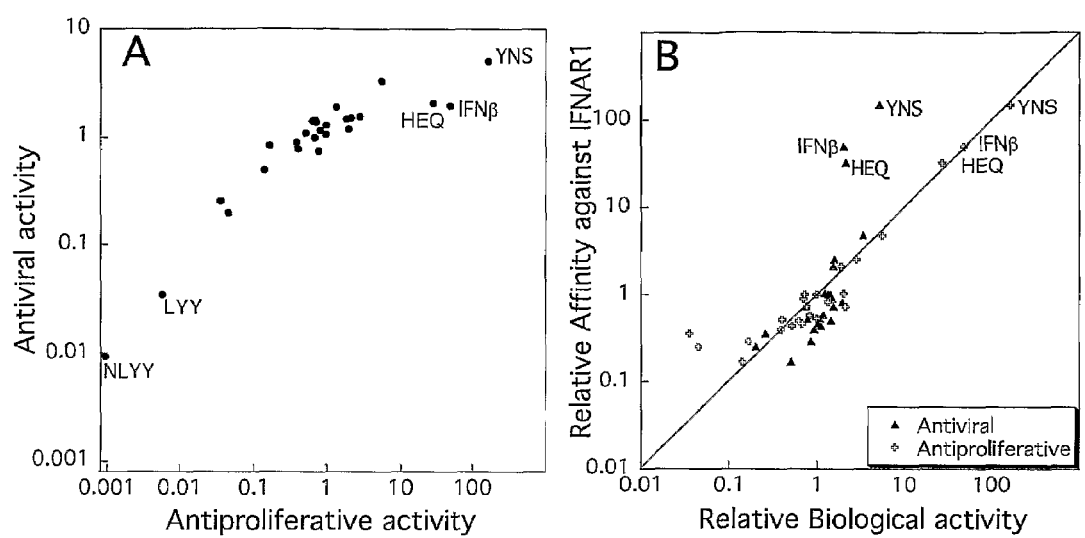
FIGS. 5A-5B show biological activities of interferon mutants.

The antiviral and antiproliferative activity of all the interferon mutant proteins was determined relative to that of wild-type IFNα2 (wt/mut) with the results being summarized in Table 2 and 4. As found with the binding affinity for IFNAR1-EC, the antiviral and antiproliferative activities did not change dramatically upon mutation. The only mutant that causes a significant increase in antiviral activity (>2-fold) is E58A. L80A, Y85A and Y89A cause a significant decrease in antiviral activity (but none over 6-fold). However, the combined LYY and NLYY mutants reduced the antiviral potency by 30 and 100-fold, respectively. This reduction roughly fits the additive effects of the single mutations (for LYY, 0.5× 0.26×0.20=0.029, similar to the result obtained for the triple-mutant). The effect on the antiproliferative activity of the same set of mutants is more significant, with both E58A and Q61A causing a significant increase in activity, while N65A, T69A, L80A, Y85A and Y89A causing a significant decrease in activity. Moreover, the magnitude of the decrease in activity as measured in the antiproliferative assay-using WISH cells are significantly larger than that measured for antiviral protection. The multiple LYY and NLYY mutants reduce activity by 190 and 1100-fold, respectively. In this case, the single mutations overestimate the effect measured for the multiple mutants by about 30-fold (for LYY, 0.14×0.035× 0.044=0.00022 versus the experimentally measured value of 0.0057, and for NLYY 0.16×0.14×0.035×0.044 0.000035 versus the experimentally measured value of 0.00092). The antiviral and antiproliferative results for all mutants analyzed are plotted in FIG. 5A. For interest, we also added the measured value for IFNβ. It seems from this graph that the antiproliferative response is much more sensitive to the specific IFNα2 mutant compared to the antiviral response. Moreover, this trend also fits the data for IFNβ, for which the antiviral activity is about 2-fold higher than that of IFNα2 (similar to the antiviral activity of the E58A mutant) while its antiproliferative activity is ~50-fold higher. Comparing the biological activity with the measured binding affinity for IFNAR1 shows that both activities generally scale with the binding affinity, but not over the whole scale (FIG. 5B).

increase in complex lifetime was observed for HEQ compared to IFNα2, and similar dissociation kinetics as for IFNβ (Table 3). In contrast, very similar association rate constants were obtained for all three species. From these data, an equilibrium dissociation constant $K_D$=83 nM was determined for the HEQ/IFNAR1-EC complex, $K_D$=33 nM was determined for the YNS/IFNAR1-EC complex, $K_D$=1.6 μM for IFNα2-wt/IFNAR1-EC complex and $K_D$=66 nM for IFNβ/IFNAR1-EC complex. The binding affinity of HEQ to IFNAR2-EC is similar to that measured for IFNα2-wt (5 nM), which is about 10 fold weaker than that of IFNβ (Table 3). Thus, only the affinity of HEQ towards IFNAR1 is similar to IFNβ, but not towards IFNAR1.

TABLE 2

Biological Activity of IFNα2 mutants

| IFN Mutant | Antiviral activity (WISH) | | | Antiproliferative activity (WISH) | | | Antiproliferative (DAUDI) | |
|---|---|---|---|---|---|---|---|---|
| | 50% (pM) | wt/mut | Slope$^a$ wt/mut | 50% (nM) | wt/mut | slope$^a$ wt/mut | 50% (pM) | wt/mut |
| wt | 0.85 | | | 1.36 | | | 0.5 | |
| H57A | 0.57 | 1.5 | 1.08 | 0.76 | 1.8 | 1.0 | 1.12 | 0.56 |
| E58A | 0.26 | 3.3 | 0.95 | 0.25 | 5.4 | 1.15 | 0.20 | 2.45 |
| Q61A | 0.45 | 1.9 | 1.04 | 0.49 | 2.8 | 1.65 | 0.54 | 0.92 |
| Q62A | 0.45 | 1.9 | | 1.05 | 1.3 | | 0.45 | 1.12 |
| F64A | 0.77 | 1.1 | | 2.72 | 0.5 | | 0.68 | 0.73 |
| N65A | 1.06 | 0.8 | 0.99 | 8.00 | 0.17 | 1.48 | 0.58 | 0.86 |
| S68A | 0.57 | 1.5 | | 0.68 | 2.0 | | 0.52 | 0.96 |
| T69A | 0.94 | 0.9 | | 3.40 | 0.4 | | 0.31 | 1.61 |
| K70A | 0.71 | 1.2 | | 1.70 | 0.8 | | 0.33 | 1.51 |
| D71A | 0.61 | 1.4 | | 1.94 | 0.7 | | 0.30 | 1.67 |
| S73A | 0.61 | 1.4 | | 2.27 | 0.6 | | 0.57 | 0.88 |
| T79A | 0.61 | 1.4 | | 1.94 | 0.7 | | 0.42 | 1.20 |
| L80A | 1.70 | 0.5 | | 9.71 | 0.14 | | 0.47 | 1.07 |
| K83A | 0.65 | 1.3 | | 1.36 | 1.0 | | 0.56 | 0.89 |
| Y85A | 3.27 | 0.26 | 1.0 | 39.0 | 0.035 | 1.84 | 1.52 | 0.33 |
| T86A | 0.77 | 1.1 | | 1.36 | 1.0 | 2.2 | 0.35 | 1.41 |
| Y89A | 4.25 | 0.20 | 1.0 | 30.0 | 0.045 | | 3.13 | 0.16 |
| Q90A | 0.71 | 1.2 | | 0.72 | 1.9 | | 0.45 | 1.11 |
| N93A | 0.85 | 1.0 | | 1.94 | 0.7 | | 0.60 | 0.84 |
| E96A | 1.06 | 0.8 | | 3.40 | 0.4 | | 1.25 | 0.4 |
| V99A | 1.13 | 0.75 | | 1.84 | 0.74 | | 0.51 | 0.98 |
| LYY | 24.29 | 0.035 | 1.32 | 238 | 0.0057 | 4.1 | | |
| NLYY | 92.39 | 0.0092 | | 1478 | 0.00092 | 3.2 | | |
| HEQ | 0.41 | 2.07 | | 0.05 | 24.18 | | | |
| α8-tail | 0.3 | 3 | | 0.13 | 10 | | | |
| IFNβ | 0.43 | 2 | 0.72 | 0.03 | 42.86 | 0.63 | | |

LYY is the triple mutant L80A, Y85A, Y89A. NLYY(SEQ ID NO: 6) is the quadruple mutant including LYY and N65A. The 50% activity point was obtained by fitting the data to Eq. 1.
$^a$The slope is from Eq. 1.

Example 4

Ternary Complex Stability is Enhanced by HEQ Compared to IFNα2

Since three mutations to Ala were found to increase binding by 2 to 4 fold, these three IFNα2 mutations (H57A, E58A, Q61A) were combined into a single IFNα2 mutant protein, as used herein, designated HEQ (SEQ ID NO: 5).

Binding of IFNs to type I Interferon receptor-extracellular domain (IFNAR1-EC), and to the ternary complex including IFNAR1-EC and IFNAR2-EC was studied by total internal reflection fluorescence spectroscopy (TIRFS). IFNAR2-EC and IFNAR1-EC were tethered through their C-terminal histidine-tags onto solid-supported lipid bilayers. The dissociation kinetics of IFNα2-wt, HEQ, and IFNβ from IFNAR1-EC as monitored by TIRFS are compared in FIG. 1C. A 20-fold IFN induces biological activity by the formation of the ternary complex (IFNAR1-IFN-IFNAR2) in a 1:1:1 stoichiometry. Because of cooperative binding to the two surface-bound receptor subunits, the apparent ligand binding affinity is higher than binding to IFNAR2 alone, and depends on the relative and absolute receptor surface concentrations (Lamken, P. et al., 2004, *J Mol Biol* 341, 303-318). Increased stability of the ternary complex by increased affinity towards IFNAR1 can be probed by the ligand dissociation kinetics. Therefore, the dissociation of IFNα2 (SEQ ID NO: 2), HEQ (SEQ ID NO: 5), YNS (SEQ ID NO: 11), α8-tail (SEQ ID NO: 7) and IFNβ (SEQ ID NO: 3) were compared at different concentrations of IFNAR1-EC and IFNAR2-EC at stoichiometric ratio. For IFNβ, measurements were done using the 147A mutant on IFNAR2, which binds IFNβ at a 5 nM affinity, similar to that of IFNα2 towards wt-IFNAR2 (Table 3). This comes to compare only the effect of IFNAR1 surface concentration on ligand dissociation. While for IFNα2, the dissociation kinetics strongly depends on the receptor surface concentration, overlaying dissociation curves were observed for IFNβ and HEQ. This clearly demonstrates the higher stability of the ternary complex formed with IFNβ and HEQ. Even at the highest receptor concentration (which is much above the cellular receptor concentration at 1000 receptors per cell), faster dissociation of IFNα2-wild-type was observed than for IFNβ and HEQ at the lowest receptor concentrations. However, if receptor-surface concentrations are increased further, eventually IFNα2-wt dissociates at comparable rates to IFNβ or HEQ. The stability of the ternary complex is a combined function of surface-receptor concentrations and of the binding affinities towards the individual receptors. Assuming that the stability of the ternary complex is related to biological activity, it is not surprising that differential activation of tighter binding IFNs can be sequestered in cells with high-receptor numbers, either natural (like in Daudi cells) or due to transfection. This also highlights the danger of transfecting cells with cell-surface receptors at non-native levels, an issue usually ignored.

TABLE 3

Rate constants and affinities of the interaction of IFNα2 wild-type, IFNβ and IFNα2 mutants with IFNAR1-EC and IFNAR2-EC

| | IFNAR1-EC | | | IFNAR2-EC | | |
|---|---|---|---|---|---|---|
| | $k_a$ [$M^{-1}s^{-1}$][a] | $k_d$ [$s^{-1}$] | $K_D$ [nM] | $k_a$ [$M^{-1}s^{-1}$] | $k_d$ [$s^{-1}$] | $K_D$ [nM][c] |
| IFNα2[a] | ~2·10$^5$ | | 1500 | 1·10$^7$ | 0.006 | 0.6 |
| IFNβ[b] | 3·10$^5$ | 0.020 | 66 | 5·10$^7$ | 0.0012 | 0.024 |
| HEQ[a] | 3·10$^5$ | 0.025 | 83 | 1·10$^7$ | 0.006 | 0.6 |
| YNS | 3·10$^5$ | 0.01 | 33 | 1·10$^7$ | 0.006 | 0.6 |
| α8-tail | | | | 7·10$^7$ | 0.002 | 0.024 |

[a]mutant S136C site-specifically labeled with Oregon Green 488 maleimide
[b]site-specifically labeled with Oregon Green 488 maleimide at the free C17 residue
[c]interaction with IFNAR2-EC I47A Example 5

Antiviral and Antiproliferative Activity of IFNα2 Mutants: HEQ, MDL, α8-Tail and YNS It has been noted that the antiviral potency of IFNβ on WISH cells is only 2-fold higher compared to IFNα2, while its antiproliferative activity is about 50-fold higher. FIGS. 4B-4C shows the antiviral and antiproliferative activities of IFNα2-wt, HEQ (SEQ ID NO: 5) and IFNβ, as measured on WISH cells. In this assays, HEQ activity profile is comparable with that of IFNβ. Despite the large increase in binding affinity of HEQ towards IFNAR1, its antiviral potency is only 2-fold higher than that of wild-type IFNα2. Its antiproliferative activity is increased by ~25 fold compared to a 42-fold increase in the antiproliferative activity of IFNβ (Table 4). The same trend is true also for MDL (SEQ ID NO: 10) and YNS (SEQ ID NO: 11). While their antiviral activity is roughly that of IFNα2, their antiviral activity is much higher. MDL presents the same activity level as IFNβ, while YNS presents an even higher level of antiproliferative activity. The increased antiproliferative activities are in line with the increased affinities of these two IFNs towards IFNAR1. As noted previously, IFNβ seems to arrest growth faster compared to IFNα2. As a result, the cell-count after applying high IFN concentrations is smaller for IFNβ. This phenomenon cannot be compensated by using higher concentration of IFNα2, but is a qualitative difference (FIG. 4B). In this aspect, HEQ and YNS behave like IFNα2-wt, and not as IFNβ. The slope of the titration curve of HEQ (which relates to the concentration dependent onset) is in-between that of wt-IFNα2 and IFNβ.

TABLE 4

Relative biological activities of IFNα2 wild-type, mutants and IFNβ

| | Anti-proliferative activity | | | | Anti-viral activity | |
|---|---|---|---|---|---|---|
| | WISH | | MDA231 | | WISH | |
| | EC50 (nM) | Ratio vs. IFNα | EC50 (nM) | Ratio vs. IFNα | EC50 (pM) | Ratio vs. IFNα |
| IFNα | 2.0 | 1 | 0.7 | 1 | 0.6 | 1 |
| IFNβ | 0.03 | 71 | 0.07 | 10 | 0.3 | 2.0 |
| YNS | 0.013 | 164 | 0.01 | 70 | 0.12 | 5.0 |
| MDL | 0.085 | 24 | | | 0.6 | 1.0 |
| HEQ | 0.06 | 35 | | | 0.3 | 2.0 |
| α8-tail | 0.2 | 10 | | | 0.2 | 3.0 |

Example 6

Monitoring Gene Activation Using Gene-Chip Technology

Gene-chips have become a standard technology to obtain complete information about differential gene-activation. Indeed, a number of studies have been conducted to investigate the gene-expression profile upon IFN induction (de Veer, M. J. et al., 2001, J Leukoc Biol. 69, 912-920). The effect of IFNs on gene expression was monitored by spotted oligonucleotide microarray experiments. WISH cells were treated for 16 hours with 0.3 nM IFNα2; 3 nM (10,000 units) IFNα2; 0.3 nM HEQ and 0.15 nM IFNβ (1,000 units). The concentrations were chosen to produce >90% of an antiproliferative response (IFNα2-wt-3 nM, HEQ and IFNβ) or under 10% of antiproliferative response (IFNα2-wt-0.3 μM) in WISH cells. In each condition the experiment of IFN-treatment versus no-treatment was performed in dye-swap microarray duplicates. In addition, four replicates of microarray experiments consisting of no-treatment versus no-treatment was used as additional control. The normalized ratio between the two colors is taken as the level of induction. The criteria chosen for defining the list of IFN-regulated genes is described in the Methods section.

Figure 6A:
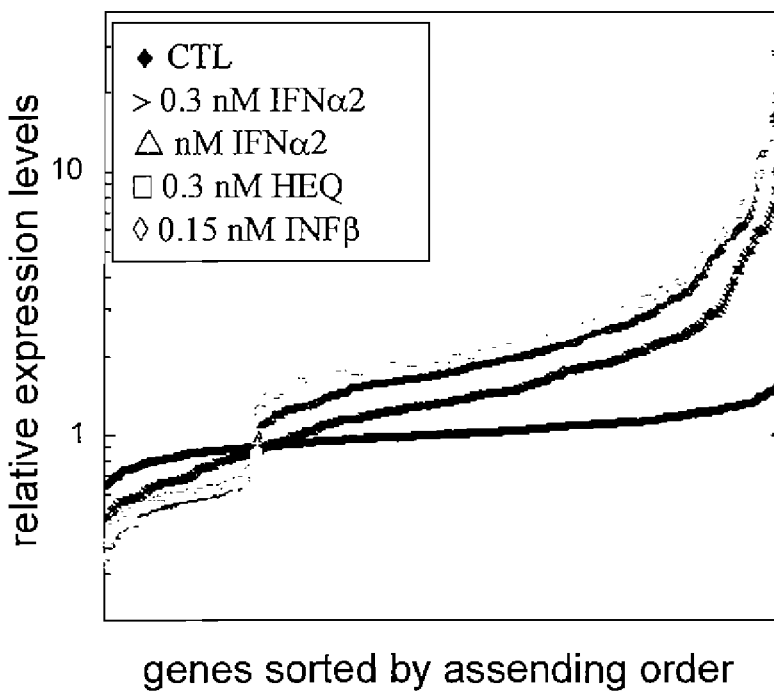
FIGS. 6A-6C show the effect of interferon on gene expression monitored by spotted oligonucletide microarray experiments. Four different 16 hours-long interferon treatments were tested: 0.3 nM (1,000 units) IFNα2-wt; 3 μM (10,000 units) IFNα2-wt; 0.3 nM HEQ (SEQ ID NO: 5) and 0.15 nM IFNβ (1,000 units). Each condition is represented by IFN-treatment versus no-treatment in dye-swap microarray duplicates. In addition, four replicates of microarray experiments consisting of no-treatment versus no-treatment from another sample represent no IFN treatment as control.

Gene-chip results can be analyzed on a per-gene basis, or looking at general trends of gene-induction. FIG. 6 comes to give an overview of the trends recorded for the change in expression levels of 395 IFN-regulated genes, 16 hr after treatment with IFNβ (0.15 nM), HEQ and IFNα2-wt (0.3 nM and 3 nM, respectively). In FIG. 6A the relative (to no treatment) expression levels of the 395 genes were plotted in ascending order according to fold-change. The black-dots are of the control chip, which contained a mixture of only untreated samples on both color-channels. This provides an estimate of the expected random fluctuation. The minimum and maximum changes in expression level recorded for the control chip were 0.65-1.6-fold, with the ratio between the two channels being only 0.75-1.4-fold for the top 95% of the genes. The low level of random fluctuation in gene-expression provides a high level of confidence in the quality of the data. In general, the gene expression levels are is similar for IFNβ (0.15 nM) and HEQ (0.3 nM) (FIG. 6A), while a much lower level of induction was recorded for IFNα2-wt (0.3 nM). Gene induction upon addition of 3 nM IFNα2-wt is in between the levels recorded for IFNα2-wt (0.3 nM) and IFNβ

Figure 6B:
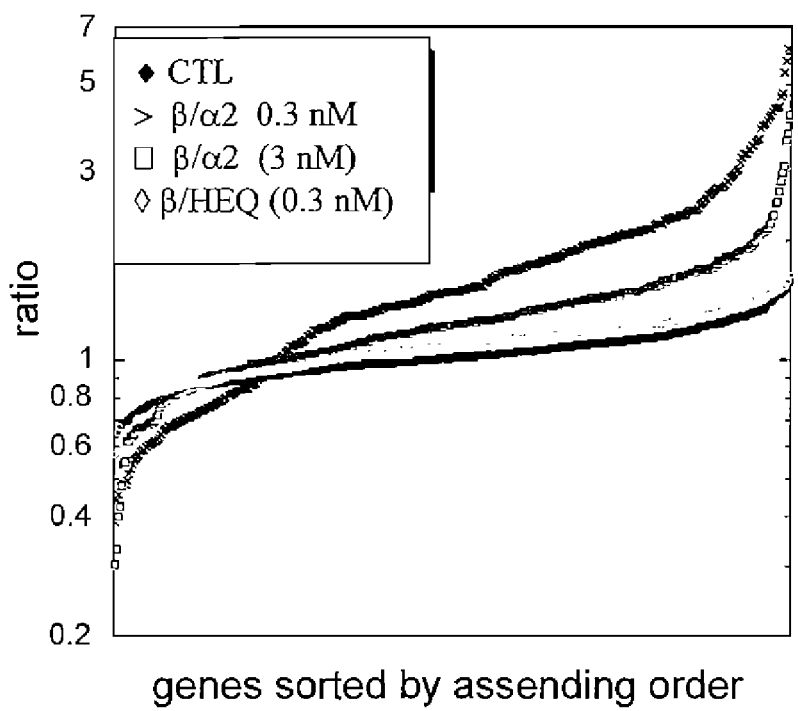

(0.15 nM) or HEQ (0.3 nM). An alternative way of analyzing the differential expression levels is to plot the ratio of change in gene activation between the different treatments (FIG. 6B). As IFNβ induced the largest change, all other values were calculated relative to IFNβ induction. The control is the same as in FIG. 6A. Again, IFNβ and HEQ seem to induce the same level of change for all genes (the green line follows the black line which is the control). This means that not a single-gene behaves significantly different upon induction with IFNβ versus HEQ. This remarkable result shows how similar both of these IFNs are. The largest differential expression is found between IFNβ and IFNα2-wt (0.3 nM). Again, the results for IFNα2-wt (3 nM) are in between those recorded for IFNα2-wt (0.3 nM) and HEQ.

Figure 6C:
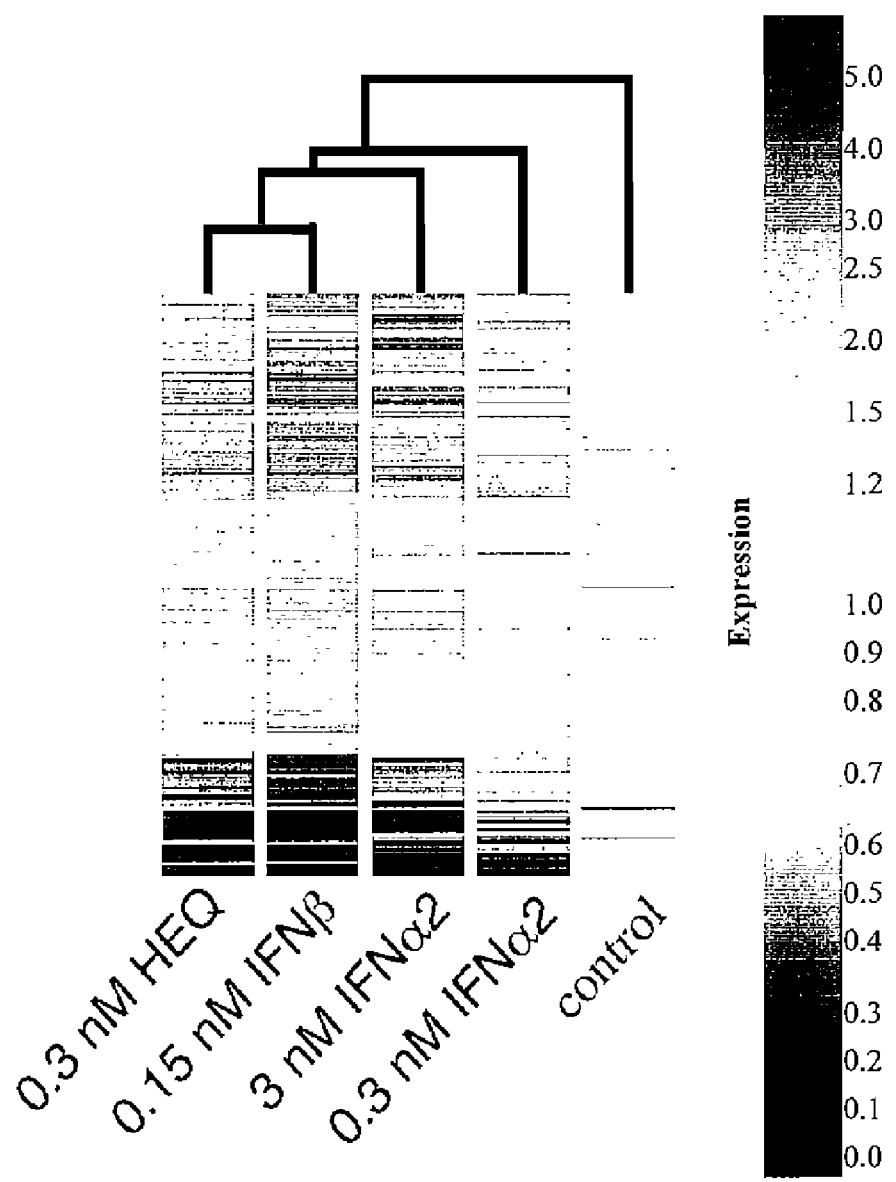

Cluster analysis of the IFN induced genes for the four treatments was done to give independent verification of the results presented graphically in FIGS. 6A and 6B. FIG. 6C shows that the gene expression profiles of IFNβ and HEQ cluster together, with a very short distance between them. The expression profile of cells treated with 3 nM IFNα2-wt clusters next, while the gene-expression profile of 0.3 nM IFNα2-wt is farther away. Gene expression profiling is in excellent agreement with the differential biological activity observed between INFβ and IFNα2, and again demonstrates that HEQ is an IFNα2 with all the characteristics of IFNβ.

Gene-chips provide detailed knowledge of the expression levels of the individual genes comprising the genome. One of the most interesting aspects of analyzing the gene expression profile of IFNβ versus IFNα2-wt is to investigate differential activation, and the relation between differential activation and IFN concentration (Der, S. D., et al., 1998, *Proc Natl Acad Sci USA* 95, 15623-15628). Out of the 395 induced genes, 59 upregulated and 9 downregulated genes were selected according to their differential level of activation between the different treatments (Jaitin et al., 2006, Mol Cell Biol 26(5): 1888-1897, Table 3).

The effect on expression of IFNβ and HEQ (SEQ ID NO: 5) on most of the genes was much stronger than the effect induced by IFNα2 at equivalent anti-viral activity concentrations, i.e. 0.15 and 0.3 nM, respectively, including many genes not influenced by IFNα2 at the 0.3 nM concentration.

Example 7

MDA231 Tumor Prevention Model

To establish sub-cutaneous (s.c.) tumors, MDA231 cells were grown in vitro to 70% confluence, trypsinized and suspended in PBS at a concentration of $10^8$ cells/ml, and $10^7$ cells were injected s.c. into the flank of a nude mouse. The mice were then randomized and separated into 3 treatment groups of 6 animals per group. The treatment regimen began on Day 1 and continued to Day 34. Mice were injected s.c. with either PBS or a specific treatment twice a week for 34 days. After 34 days of treatments the animals were sacrificed, the tumors were excised and tumor size was determined. The results are summarized in Table 5. The results clearly demonstrate that in line with the tissue culture experiments, YNS is very effective in suppressing the growth of MDA231 breast cancer cells in vivo. Following 34 days of treatment with YNS all mice treated with YNS were clean of lumps, while five out of six of the IFNα2 treated mice and all the six of the PBS treated mice had lumps of varying size.

TABLE 5

The results of MDA231 tumor prevention model

| | Treatment | | | | | | | | | | | |
|---|---|---|---|---|---|---|---|---|---|---|---|---|
| | PBS | | | | IFNα2 | | | | YNS | | | |
| Days | L | M | S | N | L | M | S | N | L | M | S | N |
| 1 | 1 | 0 | 0 | 5 | | | 4 | 2 | 0 | 0 | 6 | 0 |
| 5 | 1 | 0 | 4 | 0 | 1 | 0 | 5 | 0 | 3 | 0 | 3 | 0 |
| 8 | 1 | 2 | 2 | 0 | 1 | 0 | 5 | 0 | 3 | 2 | 1 | 0 |
| 12 | 1 | 2 | 3 | 0 | 0 | 0 | 5 | 1 | 3 | 1 | 2 | 0 |
| 15 | 3 | 2 | 3 | 0 | 0 | 0 | 5 | 1 | 1 | 3 | 0 | 2 |
| 18 | 3 | 0 | 3 | 0 | 0 | 0 | 4 | 2 | 1 | 3 | 0 | 2 |
| 22 | 3 | 1 | 2 | 0 | 0 | 0 | 4 | 2 | 1 | 0 | 0 | 3 |
| 26 | 3 | 2 | 1 | 0 | 0 | 1 | 4 | 1 | 0 | 0 | 0 | 6 |
| 29 | 3 | 2 | 1 | 0 | 0 | 1 | 3 | 2 | 0 | 0 | 0 | 6 |
| 33 | 3 | 2 | 1 | 0 | 0 | 2 | 3 | 1 | 0 | 0 | 0 | 6 |
| 34 | 3 | 2 | 1 | 0 | 1 | 2 | 2 | 1 | 0 | 0 | 0 | 6 |

Mice were injected with MDA231 cells on day zero, followed by injections of 20 μg/mice of the different treatments at the indicated times. Six mice were treated for each experimental condition. Growth of tumor was estimated by eye for all but day 34. On the last day (34) mice were sacrificed, and tumor was extracted and measured.
L, M, S and N stand for tumor size (in parenthesis is the measured diameter at day 34), L—large (>5 mm), M—medium (2.5-5 mm), S—small (<2.5 mm), N—none.

Example 8

Experimental Autoimmune Encephalomyelitis (EAE)

Experimental Autoimmune Encephalomyelitis (EAE), also known as Experimental Allergic Encephalomyelitis, is an animal model of multiple sclerosis (MS). Various EAE models are known in the art, depending on the method of induction, the strain of the animal and the antigen employed to induce the disease. EAE is an acute or chronic-relapsing, acquired, inflammatory and demyelinating autoimmune disease. Different forms of EAE resemble very closely various forms and stages of MS.

In the present study, EAE is induced by injection of Myelin Basic Protein (MBP), a method known to model the acute phase of MS. In this model the onset of the disease is observed by the appearance of clinical symptoms about 10 days after induction. The disease progresses and the clinical score increases and peaks around day 15 and spontaneous recovery is observed around day 23 after induction of the disease.

Female Lewis rats (average body weight 130-180 g, Harlan, Israel) are injected s.c. into the hind paws with 25 μg of purified guinea pig myelin basic protein (MBP, Sigma) emulsified in 0.1 ml of Complete Freund's Adjuvant (Difco). Animals are maintained on a 12-hour light/12-hour dark regimen, at a constant temperature of 22° C., with food and water ad libitum. Starting from day 8 following induction, animals are followed up on a daily basis. The results are recorded as clinical score; score of 0 indicates a normal animal with no clinical signs, 0.5 indicates a loss of tonicity in the distal part of the tail, 1 indicates whole tail paralysis, 1.5 indicates weakness in one hind leg, 2 indicates weakness in both hind legs, 2.5 indicates in one fore leg, 3 indicates paralysis of all four legs, 4 indicates complete body paralysis and moribund state and 5 indicates death. The clinical score of the animals is recorded for ~15 days following onset of disease until the end of the study 25 days following induction and the area under the curve (AUC) is calculated over this period of time.

Animals that exhibit symptom of the disease, which could be clinically scored between 0.5 and 1, are treated with compositions of HEQ (SEQ ID NO: 5), YNS (SEQ ID NO: 11) or vehicle control for three consecutive days starting from the onset of the disease (~at day 9-11 following disease induction). Several routes of administration are assessed, for example, intravenously (in vehicle) or orally by gavage (in vehicle) at volume dose of 5 ml/kg. On the last day of study (about day 25) animals are euthanized with sodium pentobarbitone 100 mg/kg i.p.

Results are expressed as mean±SEM and the differences between the treatment groups were analyzed by analysis of variance (ANOVA) followed by Tukey's post hoc test. A value of $p<0.05$ is considered to be statistically significant and is indicated on the figure by an asterisk over the relevant treatment group.

Validity of the model is established using methylprednisolone as positive control. When the steroid is administered daily for 5 consecutive days i.v. at 30 mg/kg starting from day of disease induction by MBP injection, a 34% reduction in AUC was reported.

Example 9

An Animal Model of Systemic Lupus Erythematosus (SLE)

Female (NZB X NZW)$_{F1}$ hybrid mice (referred to hereafter as "NZB/W mice") spontaneously develop a lupus-like disease characterized by the presence of serum autoantibodies to double-stranded DNA (dsDNA). These mice, which eventually experience total kidney failure, are often used as a model for experimentation directed at better understanding and treating lupus in humans. Over time, this condition in NZB/W mice progresses to kidney malfunction as manifested by the appearance of proteinuria.

Female NZB/W mice 32 weeks of age are used in an experiment to determine whether NLYY (SEQ ID NO: 6) could delay the development of lupus-like disease. The mice are divided into two groups, and each group is treated every other day with either NLYY (group of 10 mice) or rat IgG as a control (group of 10 mice), administered by intraperitoneal injection. Treatments are continued for five weeks, and the mice are assessed weekly for the presence of proteinuria.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It should be understood that the detailed description and specific examples, while indicating preferred embodiments of the invention, are given by way of illustration only, since various changes and modifications within the spirit and scope of the invention will become apparent to those skilled in the art from this detailed description.

The invention claimed is:

1. An isolated DNA molecule encoding a mutated human IFNα2 polypeptide, said IFNα2 polypeptide comprising: at least three mutations selected from the group consisting of (a) mutation of the histidine at position 57 to a residue selected from the group consisting of alanine, tyrosine, and methionine; (b) mutation of the glutamate at position 58 to a residue selected from the group consisting of alanine, asparagine, and aspartate; (c) mutation of the glutamine at position 61 to a residue selected from the group consisting of alanine, serine and leucine; (d) mutation of the glutamate at position 159 to lysine; (e) mutation of the serine at position 160 to arginine; and (f) mutation of the arginine at position 162 to lysine; or at least four mutations selected from the group consisting of: (g) mutation of the asparagine at position 65 to alanine; (h) mutation of the leucine at position 80 to alanine; (i) mutation of the tyrosine at position 85 to alanine; (j) mutation of the tyrosine at position 89 to alanine; (k) mutation of the glutamate at position 159 to lysine; (l) mutation of the serine at position 160 to arginine; and (m) mutation of the arginine at position 162 to lysine.

2. A vector comprising the DNA molecule according to claim 1, operably linked to one or more transcription control elements.

3. An isolated host cell comprising the vector of claim 2.

4. An isolated DNA molecule encoding a mutated human IFNα2 polypeptide, said IFNα2 polypeptide consisting of the sequence set forth in SEQ ID NO: 21.

5. A vector comprising the DNA molecule of claim 4.

6. The vector of claim 5, wherein said vector is capable of expressing a mutant human IFNα2 polypeptide in a prokaryotic host cell or eukaryotic host cell.

7. An isolated host cell comprising the vector of claim 5.

* * * * *

UNITED STATES PATENT AND TRADEMARK OFFICE
CERTIFICATE OF CORRECTION

PATENT NO.        : 7,767,799 B2                                    Page 1 of 1
APPLICATION NO.   : 11/994159
DATED             : August 3, 2010
INVENTOR(S)       : Schreiber et al.

It is certified that error appears in the above-identified patent and that said Letters Patent is hereby corrected as shown below:

Column 1:
Line 6, change "PCT/IL2006/754" to -- PCT/IL2006/000754 --.

Signed and Sealed this

Nineteenth Day of October, 2010

David J. Kappos
*Director of the United States Patent and Trademark Office*

UNITED STATES PATENT AND TRADEMARK OFFICE
CERTIFICATE OF CORRECTION

PATENT NO. : 7,767,799 B2
APPLICATION NO. : 11/994159
DATED : August 3, 2010
INVENTOR(S) : Schreiber et al.

Page 1 of 1

It is certified that error appears in the above-identified patent and that said Letters Patent is hereby corrected as shown below:

Column 78:
Line 45 (claim 4, line 2), change each occurrence of "IFNα2 polypeptide" to -- IFNα2 DNA molecule --.

Signed and Sealed this
Twenty-third Day of August, 2011

David J. Kappos
*Director of the United States Patent and Trademark Office*

UNITED STATES PATENT AND TRADEMARK OFFICE
CERTIFICATE OF CORRECTION

PATENT NO.        : 7,767,799 B2
APPLICATION NO.   : 11/994159
DATED             : August 3, 2010
INVENTOR(S)       : Schreiber et al.

It is certified that error appears in the above-identified patent and that said Letters Patent is hereby corrected as shown below:

Column 78, lines 44-46, Claim 4, should read:

4. An isolated DNA molecule encoding a mutated human IFNα2 polypeptide, said DNA molecule consisting of the sequence set forth in SEQ ID NO: 21.

This certificate supersedes the Certificate of Correction issued August 23, 2011.

Signed and Sealed this
Fourteenth Day of February, 2012

David J. Kappos
*Director of the United States Patent and Trademark Office*

SEQUENCE LISTING

<160> NUMBER OF SEQ ID NOS: 45

<210> SEQ ID NO 1
<211> LENGTH: 166
<212> TYPE: PRT
<213> ORGANISM: Homo sapiens

<400> SEQUENCE: 1

Cys Asp Leu Pro Gln Thr His Ser Leu Gly Asn Arg Arg Ala Leu Ile
1               5                   10                  15

Leu Leu Ala Gln Met Gly Arg Ile Pro Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Thr Trp Glu Gln Ser
65                  70                  75                  80

Leu Leu Glu Lys Phe Ser Thr Glu Leu Asn Gln Gln Leu Asn Asp Leu
                85                  90                  95

Glu Ala Cys Val Ile Gln Glu Val Gly Val Glu Glu Thr Pro Leu Met
            100                 105                 110

Asn Val Asp Ser Ile Leu Ala Val Lys Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

```
Arg Ala Glu Ile Met Arg Ser Phe Ser Leu Ser Lys Ile Phe Gln Glu
145                 150                 155                 160

Arg Leu Arg Arg Lys Glu
                165

<210> SEQ ID NO 2
<211> LENGTH: 165
<212> TYPE: PRT
<213> ORGANISM: Homo sapiens

<400> SEQUENCE: 2

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 3
<211> LENGTH: 165
<212> TYPE: PRT
<213> ORGANISM: Homo sapiens

<400> SEQUENCE: 3

Ser Tyr Asn Leu Leu Gly Phe Leu Gln Arg Ser Ser Asn Phe Gln Cys
1               5                   10                  15

Gln Lys Leu Leu Trp Gln Leu Asn Gly Arg Leu Glu Tyr Cys Leu Lys
                20                  25                  30

Asp Arg Met Asn Phe Asp Ile Pro Glu Glu Ile Lys Gln Leu Gln Gln
            35                  40                  45

Phe Gln Lys Glu Asp Ala Ala Leu Thr Ile Tyr Glu Met Leu Gln Asn
        50                  55                  60

Ile Phe Ala Ile Phe Arg Gln Asp Ser Ser Ser Thr Gly Trp Asn Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Lys Glu Asp Phe Thr Arg
            100                 105                 110

Gly Lys Leu Met Ser Ser Leu His Leu Lys Arg Tyr Tyr Gly Arg Ile
        115                 120                 125
```

```
Leu His Tyr Leu Lys Ala Lys Glu Tyr Ser His Cys Ala Trp Thr Ile
        130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 4
<211> LENGTH: 165
<212> TYPE: PRT
<213> ORGANISM: Homo sapiens

<400> SEQUENCE: 4

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp Arg
    50                  55                  60

Lys Ile Met Gln Ser Gln Ile Val Ser Phe Tyr Phe Lys Leu Phe Lys
65                  70                  75                  80

Asn Phe Lys Asp Asp Gln Ser Ile Gln Lys Ser Val Glu Thr Ile Lys
                85                  90                  95

Glu Asp Met Asn Val Lys Phe Phe Asn Ser Asn Lys Lys Lys Arg Asp
            100                 105                 110

Asp Phe Glu Lys Leu Thr Asn Tyr Ser Val Thr Asp Leu Asn Val Gln
        115                 120                 125

Arg Lys Ala Ile His Glu Leu Ile Gln Val Met Ala Glu Leu Ser Pro
    130                 135                 140

Ala Ala Lys Thr Gly Lys Arg Lys Arg Ser Gln Met Leu Phe Arg Gly
145                 150                 155                 160

Arg Arg Ala Ser Gln
                165

<210> SEQ ID NO 5
<211> LENGTH: 165
<212> TYPE: PRT
<213> ORGANISM: Artificial Sequence
<220> FEATURE:
<223> OTHER INFORMATION: HEQ

<400> SEQUENCE: 5

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Ala Ala Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
```

```
                  100                 105                 110
Glu Asp Ser Ile Leu Ala Val Arg Lys Tyr Phe Gln Arg Ile Thr Leu
            115                 120                 125
Tyr Leu Lys Glu Lys Lys Tyr Ser Pro Cys Ala Trp Glu Val Val Arg
        130                 135                 140
Ala Glu Ile Met Arg Ser Phe Ser Leu Ser Thr Asn Leu Gln Glu Ser
145                 150                 155                 160
Leu Arg Ser Lys Glu
                165

<210> SEQ ID NO 6
<211> LENGTH: 165
<212> TYPE: PRT
<213> ORGANISM: Artificial Sequence
<220> FEATURE:
<223> OTHER INFORMATION: NLYY

<400> SEQUENCE: 6

Cys Asp Leu Pro Gln Thr His Ser Leu Gly Ser Arg Arg Thr Leu Met
1               5                   10                  15
Leu Leu Ala Gln Met Arg Lys Ile Ser Leu Phe Ser Cys Leu Lys Asp
            20                  25                  30
Arg His Asp Phe Gly Phe Pro Gln Glu Glu Phe Gly Asn Gln Phe Gln
        35                  40                  45
Lys Ala Glu Thr Ile Pro Val Leu His Glu Met Ile Gln Gln Ile Phe
    50                  55                  60
Ala Leu Phe Ser Thr Lys Asp Ser Ser Ala Ala Trp Asp Glu Thr Ala
65                  70                  75                  80
Leu Asp Lys Phe Ala Thr Glu Leu Ala Gln Gln Leu Asn Asp Leu Glu
                85                  90                  95
Ala Cys Val Ile Gln Gly Val Gly Val Thr Glu Thr Pro Leu Met Lys
            100                 105                 110
Glu Asp Ser Ile Leu Ala Val Arg Lys Tyr Phe Gln Arg Ile Thr Leu
        115                 120                 125
Tyr Leu Lys Glu Lys Lys Tyr Ser Pro Cys Ala Trp Glu Val Val Arg
    130                 135                 140
Ala Glu Ile Met Arg Ser Phe Ser Leu Ser Thr Asn Leu Gln Glu Ser
145                 150                 155                 160
Leu Arg Ser Lys Glu
                165

<210> SEQ ID NO 7
<211> LENGTH: 165
<212> TYPE: PRT
<213> ORGANISM: Artificial Sequence
<220> FEATURE:
<223> OTHER INFORMATION: a8-tail

<400> SEQUENCE: 7

Cys Asp Leu Pro Gln Thr His Ser Leu Gly Ser Arg Arg Thr Leu Met
1               5                   10                  15
Leu Leu Ala Gln Met Arg Lys Ile Ser Leu Phe Ser Cys Leu Lys Asp
            20                  25                  30
Arg His Asp Phe Gly Phe Pro Gln Glu Glu Phe Gly Asn Gln Phe Gln
        35                  40                  45
Lys Ala Glu Thr Ile Pro Val Leu His Glu Met Ile Gln Gln Ile Phe
    50                  55                  60
```

```
Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Lys Arg
145                 150                 155                 160

Leu Lys Ser Lys Glu
            165

<210> SEQ ID NO 8
<211> LENGTH: 165
<212> TYPE: PRT
<213> ORGANISM: Artificial Sequence
<220> FEATURE:
<223> OTHER INFORMATION: HEQ + a8-tail

<400> SEQUENCE: 8

Cys Asp Leu Pro Gln Thr His Ser Leu Gly Ser Arg Arg Thr Leu Met
 1               5                  10                  15

Leu Leu Ala Gln Met Arg Lys Ile Ser Leu Phe Ser Cys Leu Lys Asp
                 20                  25                  30

Arg His Asp Phe Gly Phe Pro Gln Glu Glu Phe Gly Asn Gln Phe Gln
             35                  40                  45

Lys Ala Glu Thr Ile Pro Val Leu Ala Ala Met Ile Ala Gln Ile Phe
         50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Lys Arg
145                 150                 155                 160

Leu Lys Ser Lys Glu
            165

<210> SEQ ID NO 9
<211> LENGTH: 165
<212> TYPE: PRT
<213> ORGANISM: Artificial Sequence
<220> FEATURE:
<223> OTHER INFORMATION: NLYY + a8-tail

<400> SEQUENCE: 9

Cys Asp Leu Pro Gln Thr His Ser Leu Gly Ser Arg Arg Thr Leu Met
 1               5                  10                  15

Leu Leu Ala Gln Met Arg Lys Ile Ser Leu Phe Ser Cys Leu Lys Asp
                 20                  25                  30
```

```
Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
 50                  55                  60

Ala Leu Phe Ser Thr Lys Asp Ser Ser Ala Ala Trp Asp Glu Thr Ala
 65                  70                  75                  80

Leu Asp Lys Phe Ala Thr Glu Leu Ala Gln Gln Leu Asn Asp Leu Glu
                 85                  90                  95

Ala Cys Val Ile Gln Gly Val Gly Val Thr Glu Thr Pro Leu Met Lys
                100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Lys Arg
145                 150                 155                 160

Leu Lys Ser Lys Glu
                165

<210> SEQ ID NO 10
<211> LENGTH: 165
<212> TYPE: PRT
<213> ORGANISM: Artificial Sequence
<220> FEATURE:
<223> OTHER INFORMATION: MDL

<400> SEQUENCE: 10

Cys Asp Leu Pro Gln Thr His Ser Leu Gly Ser Arg Arg Thr Leu Met
 1               5                  10                  15

Leu Leu Ala Gln Met Arg Lys Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu Met Asp Met Ile Leu Gln Ile Phe
 50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
                100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 11
<211> LENGTH: 165
<212> TYPE: PRT
<213> ORGANISM: Artificial Sequence
<220> FEATURE:
<223> OTHER INFORMATION: YNS
```

-continued

```
<400> SEQUENCE: 11

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Tyr Asn Met Ile Ser Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 12
<211> LENGTH: 165
<212> TYPE: PRT
<213> ORGANISM: Artificial Sequence
<220> FEATURE:
<223> OTHER INFORMATION: MDL + a8-tail

<400> SEQUENCE: 12

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Met Asp Met Ile Leu Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Lys Arg
145                 150                 155                 160

Leu Lys Ser Lys Glu
                165
```

<210> SEQ ID NO 13
<211> LENGTH: 165
<212> TYPE: PRT
<213> ORGANISM: Artificial Sequence
<220> FEATURE:
<223> OTHER INFORMATION: YNS + a8-tail

<400> SEQUENCE: 13

```
Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Tyr Asn Met Ile Ser Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Lys Arg
145                 150                 155                 160

Leu Lys Ser Lys Glu
                165
```

<210> SEQ ID NO 14
<211> LENGTH: 69
<212> TYPE: DNA
<213> ORGANISM: Artificial Sequence
<220> FEATURE:
<223> OTHER INFORMATION: codons for the first 23 amino-acids of IFNa2

<400> SEQUENCE: 14

```
tgtgatctgc cgcagactca ctctctgggt tctcgtcgta ctctgatgct gctggctcag    60
atgcgtcgt                                                            69
```

<210> SEQ ID NO 15
<211> LENGTH: 501
<212> TYPE: DNA
<213> ORGANISM: Artificial Sequence
<220> FEATURE:
<223> OTHER INFORMATION: HEQ

<400> SEQUENCE: 15

```
atgtgtgatc tgccgcagac tcactctctg ggttctcgtc gtactctgat gctgctggct    60
cagatgcgtc gtatctctct tttctcctgc ttgaaggaca acatgacttt tggatttccc   120
caggaggagt ttggcaacca gttccaaaag gctgaaacca tccctgtcct cgctgcgatg   180
atcgcgcaga tcttcaatct cttcagcaca aaggactcat ctgctgcttg ggatgagacc   240
ctcctagaca aattctacac tgaactctac cagcagctga atgacctgga agcctgtgtg   300
atacaggggg tggggtgac agagactccc ctgatgaagg aggactccat tctggctgtg   360
aggaaatact tccaaagaat cactctctat ctgaaagaga gaaatacag cccttgtgcc   420
```

```
tgggaggttg tcagagcaga aatcatgaga tcttttttctt tgtcaacaaa cttgcaagaa    480
agtttaagaa gtaaggaatg a                                               501

<210> SEQ ID NO 16
<211> LENGTH: 501
<212> TYPE: DNA
<213> ORGANISM: Artificial Sequence
<220> FEATURE:
<223> OTHER INFORMATION: NLYY

<400> SEQUENCE: 16
atgtgtgatc tgccgcagac tcactctctg ggttctcgtc gtactctgat gctgctggct    60
cagatgcgtc gtatctctct tttctcctgc ttgaaggaca gacatgactt tggatttccc    120
caggaggagt ttggcaacca gttccaaaag gctgaaacca tccctgtcct ccatgagatg    180
atccagcaga tcttcgctct cttcagcaca aaggactcat ctgctgcttg ggatgagacc    240
gccctagaca aattcgccac tgaactcgcc cagcagctga atgacctgga agcctgtgtg    300
atacaggggg tgggggtgac agagactccc ctgatgaagg aggactccat tctggctgtg    360
aggaaatact tccaaagaat cactctctat ctgaaagaga gaaatacag cccttgtgcc     420 tgggaggttg tcagagcaga aatcatgaga tcttttttctt tgtcaacaaa cttgcaagaa    480
agtttaagaa gtaaggaatg a                                               501

<210> SEQ ID NO 17
<211> LENGTH: 501
<212> TYPE: DNA
<213> ORGANISM: Artificial Sequence
<220> FEATURE:
<223> OTHER INFORMATION: a8-tail

<400> SEQUENCE: 17
atgtgtgatc tgccgcagac tcactctctg ggttctcgtc gtactctgat gctgctggct    60
cagatgcgtc gtatctctct tttctcctgc ttgaaggaca gacatgactt tggatttccc    120
caggaggagt ttggcaacca gttccaaaag gctgaaacca tccctgtcct ccatgagatg    180
atccagcaga tcttcaatct cttcagcaca aaggactcat ctgctgcttg ggatgagacc    240
ctcctagaca aattctacac tgaactctac cagcagctga atgacctgga agcctgtgtg    300
atacaggggg tgggggtgac agagactccc ctgatgaagg aggactccat tctggctgtg    360
aggaaatact tccaaagaat cactctctat ctgaaagaga gaaatacag cccttgtgcc     420 tgggaggttg tcagagcaga aatcatgaga tcttttttctt tgtcaacaaa cttgcaaaaa    480
aggttaaaaa gtaaggaatg a                                               501

<210> SEQ ID NO 18
<211> LENGTH: 501
<212> TYPE: DNA
<213> ORGANISM: Artificial Sequence
<220> FEATURE:
<223> OTHER INFORMATION: HEQ + a8-tail

<400> SEQUENCE: 18
atgtgtgatc tgccgcagac tcactctctg ggttctcgtc gtactctgat gctgctggct    60
cagatgcgtc gtatctctct tttctcctgc ttgaaggaca gacatgactt tggatttccc    120
caggaggagt ttggcaacca gttccaaaag gctgaaacca tccctgtcct cgctgcgatg    180
atcgcgcaga tcttcaatct cttcagcaca aaggactcat ctgctgcttg ggatgagacc    240
```

```
ctcctagaca aattctacac tgaactctac cagcagctga atgacctgga agcctgtgtg        300 atacagggg tgggggtgac agagactccc ctgatgaagg aggactccat tctggctgtg         360
aggaaatact tccaaagaat cactctctat ctgaaagaga agaaatacag cccttgtgcc        420
tgggaggttg tcagagcaga aatcatgaga tcttttctt tgtcaacaaa cttgcaaaaa        480
aggttaaaaa gtaaggaatg a                                                  501
```

```
<210> SEQ ID NO 19
<211> LENGTH: 501
<212> TYPE: DNA
<213> ORGANISM: Artificial Sequence
<220> FEATURE:
<223> OTHER INFORMATION: NLYY + a8-tail

<400> SEQUENCE: 19
atgtgtgatc tgccgcagac tcactctctg ggttctcgtc gtactctgat gctgctggct        60
cagatgcgtc gtatctctct tttctcctgc ttgaaggaca gacatgactt tggatttccc       120
caggaggagt ttggcaacca gttccaaaag gctgaaacca tccctgtcct ccatgagatg       180
atccagcaga tcttcgctct cttcagcaca aaggactcat ctgctgcttg ggatgagacc       240
gccctagaca aattcgccac tgaactcgcc cagcagctga atgacctgga agcctgtgtg       300 atacagggg tgggggtgac agagactccc ctgatgaagg aggactccat tctggctgtg        360
aggaaatact tccaaagaat cactctctat ctgaaagaga agaaatacag cccttgtgcc       420
tgggaggttg tcagagcaga aatcatgaga tcttttctt tgtcaacaaa cttgcaaaaa       480
aggttaaaaa gtaaggaatg a                                                 501
```

```
<210> SEQ ID NO 20
<211> LENGTH: 501
<212> TYPE: DNA
<213> ORGANISM: Artificial Sequence
<220> FEATURE:
<223> OTHER INFORMATION: MDL

<400> SEQUENCE: 20
atgtgtgatc tgccgcagac tcactctctg ggttctcgtc gtactctgat gctgctggct        60
cagatgcgtc gtatctctct tttctcctgc ttgaaggaca gacatgactt tggatttccc       120
caggaggagt ttggcaacca gttccaaaag gctgaaacca tccctgtcct catggatatg       180
atcctacaga tcttcaatct cttcagcaca aaggactcat ctgctgcttg ggatgagacc       240
ctcctagaca aattctacac tgaactctac cagcagctga atgacctgga agcctgtgtg       300 atacagggg tgggggtgac agagactccc ctgatgaagg aggactccat tctggctgtg        360
aggaaatact tccaaagaat cactctctat ctgaaagaga agaaatacag cccttgtgcc       420
tgggaggttg tcagagcaga aatcatgaga tcttttctt tgtcaacaaa cttgcaagaa       480
agtttaagaa gtaaggaatg a                                                 501
```

```
<210> SEQ ID NO 21
<211> LENGTH: 501
<212> TYPE: DNA
<213> ORGANISM: Artificial Sequence
<220> FEATURE:
<223> OTHER INFORMATION: YNS

<400> SEQUENCE: 21
atgtgtgatc tgccgcagac tcactctctg ggttctcgtc gtactctgat gctgctggct        60
cagatgcgtc gtatctctct tttctcctgc ttgaaggaca gacatgactt tggatttccc       120
```

-continued caggaggagt tggcaacca gttccaaaag gctgaaacca tccctgtcct ctataacatg        180
atctctcaga tcttcaatct cttcagcaca aaggactcat ctgctgcttg ggatgagacc        240
ctcctagaca aattctacac tgaactctac cagcagctga atgacctgga agcctgtgtg        300 atacagggggg tggggtgac agagactccc ctgatgaagg aggactccat tctggctgtg        360
aggaaatact tccaaagaat cactctctat ctgaaagaga agaaatacag cccttgtgcc        420
tgggaggttg tcagagcaga aatcatgaga tcttttttctt tgtcaacaaa cttgcaagaa        480
agtttaagaa gtaaggaatg a                                                   501

<210> SEQ ID NO 22
<211> LENGTH: 501
<212> TYPE: DNA
<213> ORGANISM: Artificial Sequence
<220> FEATURE:
<223> OTHER INFORMATION: MDL + a8-tail

<400> SEQUENCE: 22
atgtgtgatc tgccgcagac tcactctctg ggttctcgtc gtactctgat gctgctggct        60
cagatgcgtc gtatctctct tttctcctgc ttgaaggaca gacatgactt tggatttccc        120
caggaggagt tggcaacca gttccaaaag gctgaaacca tccctgtcct catggatatg        180
atcctacaga tcttcaatct cttcagcaca aaggactcat ctgctgcttg ggatgagacc        240
ctcctagaca aattctacac tgaactctac cagcagctga atgacctgga agcctgtgtg        300 atacagggggg tggggtgac agagactccc ctgatgaagg aggactccat tctggctgtg        360
aggaaatact tccaaagaat cactctctat ctgaaagaga agaaatacag cccttgtgcc        420
tgggaggttg tcagagcaga aatcatgaga tcttttttctt tgtcaacaaa cttgcaaaaa        480
aggttaaaaa gtaaggaatg a                                                   501

<210> SEQ ID NO 23
<211> LENGTH: 501
<212> TYPE: DNA
<213> ORGANISM: Artificial Sequence
<220> FEATURE:
<223> OTHER INFORMATION: YNS + a8-tail

<400> SEQUENCE: 23
atgtgtgatc tgccgcagac tcactctctg ggttctcgtc gtactctgat gctgctggct        60
cagatgcgtc gtatctctct tttctcctgc ttgaaggaca gacatgactt tggatttccc        120
caggaggagt tggcaacca gttccaaaag gctgaaacca tccctgtcct ctataacatg        180
atctctcaga tcttcaatct cttcagcaca aaggactcat ctgctgcttg ggatgagacc        240
ctcctagaca aattctacac tgaactctac cagcagctga atgacctgga agcctgtgtg        300 atacagggggg tggggtgac agagactccc ctgatgaagg aggactccat tctggctgtg        360
aggaaatact tccaaagaat cactctctat ctgaaagaga agaaatacag cccttgtgcc        420
tgggaggttg tcagagcaga aatcatgaga tcttttttctt tgtcaacaaa cttgcaaaaa        480
aggttaaaaa gtaaggaatg a                                                   501

<210> SEQ ID NO 24
<211> LENGTH: 165
<212> TYPE: PRT
<213> ORGANISM: Artificial Sequence
<220> FEATURE:
<223> OTHER INFORMATION: H57A

<400> SEQUENCE: 24

```
Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Ala Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
                165
```

<210> SEQ ID NO 25
<211> LENGTH: 165
<212> TYPE: PRT
<213> ORGANISM: Artificial Sequence
<220> FEATURE:
<223> OTHER INFORMATION: E58A

<400> SEQUENCE: 25

```
Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Ala Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
                165
```

```
<210> SEQ ID NO 26
<211> LENGTH: 165
<212> TYPE: PRT
<213> ORGANISM: Artificial Sequence
<220> FEATURE:
<223> OTHER INFORMATION: Q61A

<400> SEQUENCE: 26

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Ala Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 27
<211> LENGTH: 165
<212> TYPE: PRT
<213> ORGANISM: Artificial Sequence
<220> FEATURE:
<223> OTHER INFORMATION: H57Y

<400> SEQUENCE: 27

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu Tyr Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140
```

```
Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 28
<211> LENGTH: 165
<212> TYPE: PRT
<213> ORGANISM: Artificial Sequence
<220> FEATURE:
<223> OTHER INFORMATION: E58N

<400> SEQUENCE: 28

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Asn Met Ile Gln Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 29
<211> LENGTH: 165
<212> TYPE: PRT
<213> ORGANISM: Artificial Sequence
<220> FEATURE:
<223> OTHER INFORMATION: Q61S

<400> SEQUENCE: 29

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Ser Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110
```

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu
            165

<210> SEQ ID NO 30
<211> LENGTH: 501
<212> TYPE: DNA
<213> ORGANISM: Artificial Sequence
<220> FEATURE:
<223> OTHER INFORMATION: H57A

<400> SEQUENCE: 30
atgtgtgatc tgccgcagac tcactctctg ggttctcgtc gtactctgat gctgctggct    60
cagatgcgtc gtatctctct tttctcctgc ttgaaggaca gacatgactt tggatttccc   120
caggaggagt ttggcaacca gttccaaaag gctgaaacca tccctgtcct cgctgagatg   180
atccagcaga tcttcaatct cttcagcaca aaggactcat ctgctgcttg ggatgagacc   240
ctcctagaca aattctacac tgaactctac cagcagctga atgacctgga agcctgtgtg   300 atacagggg tgggggtgac agagactccc ctgatgaagg aggactccat tctggctgtg   360
aggaaatact tccaaagaat cactctctat ctgaaagaga gaaaatacag cccttgtgcc   420
tgggaggttg tcagagcaga aatcatgaga tcttttttctt tgtcaacaaa cttgcaagaa   480
agtttaagaa gtaaggaatg a                                             501

<210> SEQ ID NO 31
<211> LENGTH: 501
<212> TYPE: DNA
<213> ORGANISM: Artificial Sequence
<220> FEATURE:
<223> OTHER INFORMATION: E58A

<400> SEQUENCE: 31
atgtgtgatc tgccgcagac tcactctctg ggttctcgtc gtactctgat gctgctggct    60
cagatgcgtc gtatctctct tttctcctgc ttgaaggaca gacatgactt tggatttccc   120
caggaggagt ttggcaacca gttccaaaag gctgaaacca tccctgtcct ccatgcgatg   180
atccagcaga tcttcaatct cttcagcaca aaggactcat ctgctgcttg ggatgagacc   240
ctcctagaca aattctacac tgaactctac cagcagctga atgacctgga agcctgtgtg   300 atacagggg tgggggtgac agagactccc ctgatgaagg aggactccat tctggctgtg   360
aggaaatact tccaaagaat cactctctat ctgaaagaga gaaaatacag cccttgtgcc   420
tgggaggttg tcagagcaga aatcatgaga tcttttttctt tgtcaacaaa cttgcaagaa   480
agtttaagaa gtaaggaatg a                                             501

<210> SEQ ID NO 32
<211> LENGTH: 501
<212> TYPE: DNA
<213> ORGANISM: Artificial Sequence
<220> FEATURE:
<223> OTHER INFORMATION: Q61A

<400> SEQUENCE: 32

```
atgtgtgatc tgccgcagac tcactctctg ggttctcgtc gtactctgat gctgctggct      60
cagatgcgtc gtatctctct tttctcctgc ttgaaggaca gacatgactt tggatttccc     120
caggaggagt ttggcaacca gttccaaaag gctgaaacca tccctgtcct ccatgagatg     180
atcgcgcaga tcttcaatct cttcagcaca aaggactcat ctgctgcttg ggatgagacc     240
ctcctagaca aattctacac tgaactctac cagcagctga atgacctgga agcctgtgtg     300 atacagggggg tggggtgac agagactccc ctgatgaagg aggactccat tctggctgtg     360
aggaaatact tccaaagaat cactctctat ctgaaagaga agaaatacag cccttgtgcc     420
tgggaggttg tcagagcaga aatcatgaga tcttttttctt tgtcaacaaa cttgcaagaa     480
agtttaagaa gtaaggaatg a                                                 501
```

<210> SEQ ID NO 33
<211> LENGTH: 501
<212> TYPE: DNA
<213> ORGANISM: Artificial Sequence
<220> FEATURE:
<223> OTHER INFORMATION: H57Y

<400> SEQUENCE: 33

```
atgtgtgatc tgccgcagac tcactctctg ggttctcgtc gtactctgat gctgctggct      60
cagatgcgtc gtatctctct tttctcctgc ttgaaggaca gacatgactt tggatttccc     120
caggaggagt ttggcaacca gttccaaaag gctgaaacca tccctgtcct ctatgagatg     180
atccagcaga tcttcaatct cttcagcaca aaggactcat ctgctgcttg ggatgagacc     240
ctcctagaca aattctacac tgaactctac cagcagctga atgacctgga agcctgtgtg     300 atacagggggg tggggtgac agagactccc ctgatgaagg aggactccat tctggctgtg     360
aggaaatact tccaaagaat cactctctat ctgaaagaga agaaatacag cccttgtgcc     420
tgggaggttg tcagagcaga aatcatgaga tcttttttctt tgtcaacaaa cttgcaagaa     480
agtttaagaa gtaaggaatg a                                                 501
```

<210> SEQ ID NO 34
<211> LENGTH: 501
<212> TYPE: DNA
<213> ORGANISM: Artificial Sequence
<220> FEATURE:
<223> OTHER INFORMATION: E58N

<400> SEQUENCE: 34

```
atgtgtgatc tgccgcagac tcactctctg ggttctcgtc gtactctgat gctgctggct      60
cagatgcgtc gtatctctct tttctcctgc ttgaaggaca gacatgactt tggatttccc     120
caggaggagt ttggcaacca gttccaaaag gctgaaacca tccctgtcct cataacatg      180 atccagcaga tcttcaatct cttcagcaca aaggactcat ctgctgcttg ggatgagacc     240
ctcctagaca aattctacac tgaactctac cagcagctga atgacctgga agcctgtgtg     300 atacagggggg tggggtgac agagactccc ctgatgaagg aggactccat tctggctgtg     360
aggaaatact tccaaagaat cactctctat ctgaaagaga agaaatacag cccttgtgcc     420
tgggaggttg tcagagcaga aatcatgaga tcttttttctt tgtcaacaaa cttgcaagaa     480
agtttaagaa gtaaggaatg a                                                 501
```

<210> SEQ ID NO 35
<211> LENGTH: 501
<212> TYPE: DNA
<213> ORGANISM: Artificial Sequence

<220> FEATURE:
<223> OTHER INFORMATION: Q61S

<400> SEQUENCE: 35

```
atgtgtgatc tgccgcagac tcactctctg ggttctcgtc gtactctgat gctgctggct      60
cagatgcgtc gtatctctct tttctcctgc ttgaaggaca cacatgactt tggatttccc     120
caggaggagt ttggcaacca gttccaaaag gctgaaacca tccctgtcct ccatgagatg     180
atctctcaga tcttcaatct cttcagcaca aaggactcat ctgctgcttg ggatgagacc     240
ctcctagaca aattctacac tgaactctac cagcagctga atgacctgga agcctgtgtg     300
atacaggggg tgggggtgac agagactccc ctgatgaagg aggactccat tctggctgtg     360
aggaaatact ccaaagaat cactctctat ctgaaagaga gaaatacag cccttgtgcc     420
tgggaggttg tcagagcaga atcatgaga tcttttttctt tgtcaacaaa cttgcaagaa     480
agtttaagaa gtaaggaatg a                                               501
```

<210> SEQ ID NO 36
<211> LENGTH: 166
<212> TYPE: PRT
<213> ORGANISM: Homo sapiens

<400> SEQUENCE: 36

```
Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn Gln Phe
        35                  40                  45

Gln Lys Ala Glu Ala Ile Ser Val Leu His Glu Val Ile Gln Gln Thr
    50                  55                  60

Phe Asn Leu Phe Ser Thr Lys Asp Ser Ser Val Ala Trp Asp Glu Arg
65                  70                  75                  80

Leu Leu Asp Lys Leu Tyr Thr Glu Leu Tyr Gln Gln Leu Asn Asp Leu
                85                  90                  95

Glu Ala Cys Val Met Gln Glu Val Trp Val Gly Gly Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Ser Ser Arg Asn Leu Gln Glu
145                 150                 155                 160

Arg Leu Arg Arg Lys Glu
                165
```

<210> SEQ ID NO 37
<211> LENGTH: 166
<212> TYPE: PRT
<213> ORGANISM: Homo sapiens

<400> SEQUENCE: 37

```
Cys Asp Leu Pro Glu Thr His Ser Leu Asp Asn Arg Arg Thr Met Met
1               5                   10                  15

Leu Leu Ala Gln Met Ser Arg Ile Ser Pro Ser Ser Cys Leu Met Asp
            20                  25                  30

Arg His Asp Phe Arg Phe Pro Gln Glu Glu Phe Asp Gly Asn Gln Phe
```

```
              35                  40                  45
Gln Lys Ala Pro Ala Ile Ser Val Leu His Glu Leu Ile Gln Gln Ile
         50                  55                  60
Phe Asn Leu Phe Thr Thr Lys Asp Ser Ser Ala Ala Trp Asp Glu Asp
 65                  70                  75                  80
Leu Leu Asp Lys Phe Cys Thr Glu Leu Tyr Gln Gln Leu Asn Asp Leu
                 85                  90                  95
Glu Ala Cys Val Met Gln Glu Glu Arg Val Gly Glu Thr Pro Leu Met
                100                 105                 110
Asn Ala Asp Ser Ile Leu Ala Val Lys Lys Tyr Phe Arg Arg Ile Thr
            115                 120                 125
Leu Tyr Leu Thr Glu Lys Lys Tyr Ser Pro Cys Ala Trp Glu Val Val
        130                 135                 140
Arg Ala Glu Ile Met Arg Ser Leu Ser Leu Ser Thr Asn Leu Gln Glu
145                 150                 155                 160
Arg Leu Arg Arg Lys Glu
                165

<210> SEQ ID NO 38
<211> LENGTH: 167
<212> TYPE: PRT
<213> ORGANISM: Homo sapiens

<400> SEQUENCE: 38

Cys Asp Leu Pro Gln Thr His Ser Leu Gly Asn Arg Arg Ala Leu Ile
 1               5                  10                  15
Leu Leu Ala Gln Met Gly Arg Ile Ser Pro Phe Ser Cys Leu Lys Asp
                20                  25                  30
Arg His Asp Phe Gly Phe Pro Gln Glu Glu Phe Asp Gly Asn Gln Phe
            35                  40                  45
Gln Lys Ala Gln Ala Ile Ser Val Leu His Glu Met Ile Gln Gln Thr
         50                  55                  60
Phe Asn Leu Phe Ser Thr Lys Asp Ser Ser Ala Thr Trp Glu Gln Ser
 65                  70                  75                  80
Leu Leu Glu Lys Phe Ser Thr Glu Leu Asn Gln Gln Leu Asn Asp Met
                 85                  90                  95
Glu Ala Cys Val Ile Gln Glu Val Gly Val Glu Thr Pro Leu Met
                100                 105                 110
Asn Val Asp Ser Ile Leu Ala Val Lys Lys Tyr Phe Gln Arg Ile Thr
            115                 120                 125
Leu Tyr Leu Thr Glu Lys Lys Tyr Ser Pro Cys Ala Trp Glu Val Val
        130                 135                 140
Arg Ala Glu Ile Met Arg Ser Phe Ser Leu Ser Lys Ile Phe Gln Glu
145                 150                 155                 160
Arg Leu Arg Arg Lys Glu Glx
                165

<210> SEQ ID NO 39
<211> LENGTH: 166
<212> TYPE: PRT
<213> ORGANISM: Homo sapiens

<400> SEQUENCE: 39

Cys Asp Leu Pro Gln Thr His Ser Leu Gly Asn Arg Arg Ala Leu Ile
 1               5                  10                  15
Leu Leu Ala Gln Met Gly Arg Ile Ser His Phe Ser Cys Leu Lys Asp
```

-continued

```
                    20                  25                  30
Arg His Asp Phe Gly Phe Pro Glu Glu Phe Asp Gly His Gln Phe
                35                  40                  45

Gln Lys Thr Gln Ala Ile Ser Val Leu His Glu Met Ile Gln Gln Thr
 50                  55                  60

Phe Asn Leu Phe Ser Thr Glu Asp Ser Ser Ala Ala Trp Glu Gln Ser
 65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Thr Pro Leu Met
                100                 105                 110

Asn Val Asp Ser Ile Leu Ala Val Arg Lys Tyr Phe Gln Arg Ile Thr
                115                 120                 125

Leu Tyr Leu Thr Glu Lys Lys Tyr Ser Pro Cys Ala Trp Glu Val Val
                130                 135                 140

Arg Ala Glu Ile Met Arg Ser Leu Ser Phe Ser Thr Asn Leu Gln Lys
145                 150                 155                 160

Arg Leu Arg Arg Lys Asp
                165
```

<210> SEQ ID NO 40
<211> LENGTH: 166
<212> TYPE: PRT
<213> ORGANISM: Homo sapiens

<400> SEQUENCE: 40

```
Cys Asp Leu Pro Gln Thr His Ser Leu Arg Asn Arg Arg Ala Leu Ile
 1                   5                  10                  15

Leu Leu Ala Gln Met Gly Arg Ile Ser Pro Phe Ser Cys Leu Lys Asp
                20                  25                  30

Arg His Glu Phe Arg Phe Pro Glu Glu Phe Asp Gly His Gln Phe
                35                  40                  45

Gln Lys Thr Gln Ala Ile Ser Val Leu His Glu Met Ile Gln Gln Thr
 50                  55                  60

Phe Asn Leu Phe Ser Thr Glu Asp Ser Ser Ala Ala Trp Glu Gln Ser
 65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
                100                 105                 110

Asn Glu Asp Phe Ile Leu Ala Val Arg Lys Tyr Phe Gln Arg Ile Thr
                115                 120                 125

Leu Tyr Leu Met Glu Lys Lys Tyr Ser Pro Cys Ala Trp Glu Val Val
                130                 135                 140

Arg Ala Glu Ile Met Arg Ser Phe Ser Phe Ser Thr Asn Leu Gln Glu
145                 150                 155                 160

Ser Leu Arg Ser Lys Glu
                165
```

<210> SEQ ID NO 41
<211> LENGTH: 166
<212> TYPE: PRT
<213> ORGANISM: Homo sapiens

<400> SEQUENCE: 41

Cys Asp Leu Pro Gln Thr His Ser Leu Gly Asn Arg Arg Ala Leu Ile

```
            1               5                  10                 15
Leu Leu Gly Gln Met Gly Arg Ile Ser Pro Phe Ser Cys Leu Lys Asp
                20                 25                 30

Arg His Asp Phe Arg Ile Pro Gln Glu Glu Phe Asp Gly Asn Gln Phe
                35                 40                 45

Gln Lys Ala Gln Ala Ile Ser Val Leu His Glu Met Ile Gln Gln Thr
        50                 55                 60

Phe Asn Leu Phe Ser Thr Glu Asp Ser Ser Ala Ala Trp Glu Gln Ser
65                     70                 75                 80

Leu Leu Glu Lys Phe Ser Thr Glu Leu Tyr Gln Gln Leu Asn Asp Leu
                85                 90                 95

Glu Ala Cys Val Ile Gln Glu Val Gly Val Glu Glu Thr Pro Leu Met
                100                105                110

Asn Glu Asp Ser Ile Leu Ala Val Arg Lys Tyr Phe Gln Arg Ile Thr
                115                120                125

Leu Tyr Leu Ile Glu Arg Lys Tyr Ser Pro Cys Ala Trp Glu Val Val
            130                135                140

Arg Ala Glu Ile Met Arg Ser Leu Ser Phe Ser Thr Asn Leu Gln Lys
145                150                155                160

Arg Leu Arg Arg Lys Glu
                165

<210> SEQ ID NO 42
<211> LENGTH: 166
<212> TYPE: PRT
<213> ORGANISM: Homo sapiens

<400> SEQUENCE: 42

Cys Asn Leu Ser Gln Thr His Ser Leu Asn Asn Arg Arg Thr Leu Met
1               5                  10                 15

Leu Met Ala Gln Met Arg Arg Ile Ser Pro Phe Ser Cys Leu Lys Asp
                20                 25                 30

Arg His Asp Phe Glu Phe Pro Gln Glu Glu Phe Asp Gly Asn Gln Phe
                35                 40                 45

Gln Lys Ala Gln Ala Ile Ser Val Leu His Glu Met Met Gln Gln Thr
        50                 55                 60

Phe Asn Leu Phe Ser Thr Lys Asn Ser Ser Ala Ala Trp Asp Glu Thr
65                     70                 75                 80

Leu Leu Glu Lys Phe Tyr Ile Glu Leu Phe Gln Gln Met Asn Asp Leu
                85                 90                 95

Glu Ala Cys Val Ile Gln Glu Val Gly Val Glu Glu Thr Pro Leu Met
                100                105                110

Asn Glu Asp Ser Ile Leu Ala Val Lys Lys Tyr Phe Gln Arg Ile Thr
                115                120                125

Leu Tyr Leu Met Glu Lys Lys Tyr Ser Pro Cys Ala Trp Glu Val Val
            130                135                140

Arg Ala Glu Ile Met Arg Ser Phe Ser Phe Ser Thr Asn Leu Gln Lys
145                150                155                160

Arg Leu Arg Arg Lys Glu
                165

<210> SEQ ID NO 43
<211> LENGTH: 166
<212> TYPE: PRT
<213> ORGANISM: Homo sapiens
```

<400> SEQUENCE: 43

```
Cys Asp Leu Pro Gln Thr His Ser Leu Gly Asn Arg Arg Ala Leu Ile
1               5                   10                  15
Leu Leu Ala Gln Met Gly Arg Ile Ser His Phe Ser Cys Leu Lys Asp
            20                  25                  30
Arg Tyr Asp Phe Gly Phe Pro Gln Glu Val Phe Asp Gly Asn Gln Phe
        35                  40                  45
Gln Lys Ala Gln Ala Ile Ser Ala Phe His Glu Met Ile Gln Gln Thr
    50                  55                  60
Phe Asn Leu Phe Ser Thr Lys Asp Ser Ser Ala Ala Trp Asp Glu Thr
65                  70                  75                  80
Leu Leu Asp Lys Phe Tyr Ile Glu Leu Phe Gln Gln Leu Asn Asp Leu
                85                  90                  95
Glu Ala Cys Val Thr Gln Glu Val Gly Val Glu Glu Ile Ala Leu Met
            100                 105                 110
Asn Glu Asp Ser Ile Leu Ala Val Arg Lys Tyr Phe Gln Arg Ile Thr
        115                 120                 125
Leu Tyr Leu Met Gly Lys Lys Tyr Ser Pro Cys Ala Trp Glu Val Val
    130                 135                 140
Arg Ala Glu Ile Met Arg Ser Phe Ser Phe Ser Thr Asn Leu Gln Lys
145                 150                 155                 160
Gly Leu Arg Arg Lys Glu
                165
```

<210> SEQ ID NO 44
<211> LENGTH: 166
<212> TYPE: PRT
<213> ORGANISM: Homo sapiens

<400> SEQUENCE: 44

```
Cys Asp Leu Pro Gln Thr His Ser Leu Gly Asn Arg Arg Ala Leu Ile
1               5                   10                  15
Leu Leu Ala Gln Met Arg Arg Ile Ser Pro Phe Ser Cys Leu Lys Asp
            20                  25                  30
Arg His Asp Phe Glu Phe Pro Gln Glu Glu Phe Asp Asp Lys Gln Phe
        35                  40                  45
Gln Lys Ala Gln Ala Ile Ser Val Leu His Glu Met Ile Gln Gln Thr
    50                  55                  60
Phe Asn Leu Phe Ser Thr Lys Asp Ser Ser Ala Ala Leu Asp Glu Thr
65                  70                  75                  80
Leu Leu Asp Glu Phe Tyr Ile Glu Leu Asp Gln Gln Leu Asn Asp Leu
                85                  90                  95
Glu Ser Cys Val Met Gln Glu Val Gly Val Ile Glu Ser Pro Leu Met
            100                 105                 110
Tyr Glu Asp Ser Ile Leu Ala Val Arg Lys Tyr Phe Gln Arg Ile Thr
        115                 120                 125
Leu Tyr Leu Thr Glu Lys Lys Tyr Ser Ser Cys Ala Trp Glu Val Val
    130                 135                 140
Arg Ala Glu Ile Met Arg Ser Phe Ser Leu Ser Ile Asn Leu Gln Lys
145                 150                 155                 160
Arg Leu Lys Ser Lys Glu
                165
```

<210> SEQ ID NO 45
<211> LENGTH: 172

```
<212> TYPE: PRT
<213> ORGANISM: Homo sapiens

<400> SEQUENCE: 45

Cys Asp Leu Pro Gln Asn His Gly Leu Leu Ser Arg Asn Thr Leu Val
1               5                   10                  15

Leu Leu His Gln Met Arg Arg Ile Ser Pro Phe Leu Cys Leu Lys Asp
            20                  25                  30

Arg Arg Asp Phe Arg Phe Pro Gln Glu Met Val Lys Gly Ser Gln Leu
        35                  40                  45

Gln Lys Ala His Val Met Ser Val Leu His Glu Met Leu Gln Gln Ile
    50                  55                  60

Phe Ser Leu Phe His Thr Glu Arg Ser Ser Ala Ala Trp Asn Met Thr
65                  70                  75                  80

Leu Leu Asp Gln Leu His Thr Gly Leu His Gln Gln Leu Gln His Leu
                85                  90                  95

Glu Thr Cys Leu Leu Gln Val Val Gly Glu Gly Glu Ser Ala Gly Ala
            100                 105                 110

Ile Ser Ser Pro Ala Leu Thr Leu Arg Arg Tyr Phe Gln Gly Ile Arg
        115                 120                 125

Val Tyr Leu Lys Glu Lys Lys Tyr Ser Asp Cys Ala Trp Glu Val Val
    130                 135                 140

Arg Met Glu Ile Met Lys Ser Leu Phe Leu Ser Thr Asn Met Gln Glu
145                 150                 155                 160

Arg Leu Arg Ser Lys Asp Arg Asp Leu Gly Ser Ser
                165                 170
```